(12) United States Patent
Miura et al.

(10) Patent No.: US 11,014,910 B2
(45) Date of Patent: May 25, 2021

(54) METHYLLACTAM RING COMPOUND AND PHARMACEUTICAL USE THEREOF

(71) Applicant: Japan Tobacco Inc., Tokyo (JP)

(72) Inventors: Tomoya Miura, Osaka (JP); Yoshinori Tamatani, Osaka (JP)

(73) Assignee: JAPAN TOBACCO INC., Tokyo (JP)

( * ) Notice: Subject to any disclaimer, the term of this patent is extended or adjusted under 35 U.S.C. 154(b) by 0 days.

(21) Appl. No.: 16/289,500

(22) Filed: Feb. 28, 2019

(65) Prior Publication Data

US 2019/0352284 A1 Nov. 21, 2019

(30) Foreign Application Priority Data

Mar. 1, 2018 (JP) .............................. JP2018-036307

(51) Int. Cl.
*C07D 403/12* (2006.01)
*A61P 3/10* (2006.01)

(52) U.S. Cl.
CPC .............. *C07D 403/12* (2013.01); *A61P 3/10* (2018.01)

(58) Field of Classification Search
CPC .................................. C07D 403/12; A61P 3/10
See application file for complete search history.

(56) References Cited

U.S. PATENT DOCUMENTS

| 5,420,141 | A | 5/1995 | Boigegrain | |
|---|---|---|---|---|
| 5,624,941 | A | 4/1997 | Barth | |
| 8,846,746 | B2 * | 9/2014 | Miura .................. | C07D 403/14 514/407 |
| 2006/0128685 | A1 | 6/2006 | Kanaya | |
| 2007/0219210 | A1 | 9/2007 | Kanaya | |
| 2008/0027014 | A1 | 1/2008 | Nomura | |
| 2013/0085132 | A1 | 4/2013 | Miura | |
| 2016/0256440 | A1 | 9/2016 | Short | |
| 2018/0346449 | A1 | 12/2018 | Miura | |
| 2019/0330193 | A1 | 10/2019 | Miura et al. | |

FOREIGN PATENT DOCUMENTS

| AU | 2004200420 A1 | 9/2004 |
|---|---|---|
| EP | 1889842 A1 | 2/2008 |
| JP | H04247081 | 9/1992 |
| JP | 2007332034 A | 12/2007 |
| JP | 2008007405 A | 1/2008 |
| JP | 2009544572 A | 12/2009 |
| WO | WO2004069824 A1 | 8/2004 |
| WO | WO2004089937 A1 | 10/2004 |
| WO | WO2004110351 A2 | 12/2004 |
| WO | WO2004110351 A3 | 4/2005 |
| WO | WO2005049578 A1 | 6/2005 |
| WO | WO2005063737 A1 | 7/2005 |
| WO | WO2006017055 A2 | 2/2006 |
| WO | WO2006054057 A2 | 5/2006 |
| WO | WO2006054057 A3 | 7/2006 |
| WO | WO2006017055 A3 | 8/2006 |
| WO | WO2007034279 A2 | 3/2007 |
| WO | WO2007098826 A2 | 9/2007 |
| WO | WO2007098826 A3 | 2/2008 |
| WO | WO2008061795 A2 | 5/2008 |
| WO | WO2008061796 A2 | 5/2008 |
| WO | WO2008061795 A3 | 7/2008 |
| WO | WO2008087529 A1 | 7/2008 |
| WO | WO2008061796 A3 | 7/2009 |
| WO | WO2009091813 A1 | 7/2009 |
| WO | WO2010007046 A2 | 1/2010 |
| WO | WO2010007046 A3 | 7/2010 |
| WO | WO2011126903 A2 | 10/2011 |
| WO | WO2011126903 A3 | 2/2012 |
| WO | WO2013031922 A1 | 3/2013 |

OTHER PUBLICATIONS

International Search Report and Written Opinion dated Jun. 18, 2019 for PCT Application No. PCT/JP2019/014721 filed on Apr. 3, 2019, 8 pages. English Translation of ISR.
International Search Report and Written Opinion dated May 21, 2019 for PCT Application No. PCT/JP2019/007799 filed on Feb. 28, 2019, 9 pages. English Translation of ISR.
U.S. Appl. No. 16/374,460, filed Apr. 3, 2019. (not submitted herewith pursuant to the waiver of 37 C.F.R. § 1.98(a)(2)(iii) issued by the Office on Sep. 21, 2004).
U.S. Appl. No. 16/677,523, for Miura et al., filed Nov. 7, 2019. (not submitted herewith pursuant to the waiver of 37 C.F.R. § 1.98(a)(2)(iii) issued by the Office on Sep. 21, 2004).

(Continued)

*Primary Examiner* — Kamal A Saeed
(74) *Attorney, Agent, or Firm* — Morrison & Foerster LLP

(57) ABSTRACT

An object of the present invention is to provide a methyllactam ring compound that has an SGLT1 inhibitory activity and is useful for a drug, or a pharmaceutically acceptable salt thereof, a pharmaceutical composition comprising it, and pharmaceutical use thereof. A compound of Formula [I]:

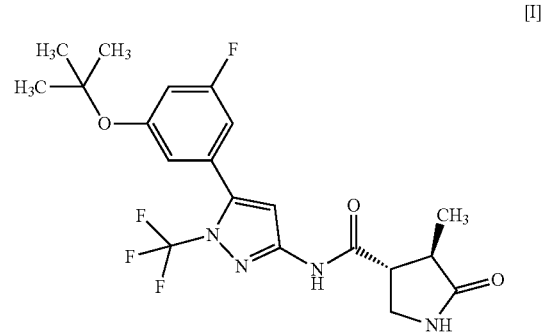

[I]

or a pharmaceutically acceptable salt thereof, a pharmaceutical composition comprising it, and pharmaceutical use thereof is provided.

10 Claims, 2 Drawing Sheets

(56) References Cited

OTHER PUBLICATIONS

Written Opinion dated Jun. 18, 2019 for PCT Application No. PCT/JP2019/014721 filed on Apr. 3, 2019, 4 pages. English Translation of WOISA Written Opinion dated May 21, 2019 for PCT Application No. PCT/JP20191007799 filed on Feb. 28, 2019, 5 pages. English Translation of WOISA.

* cited by examiner

[Fig. 1]
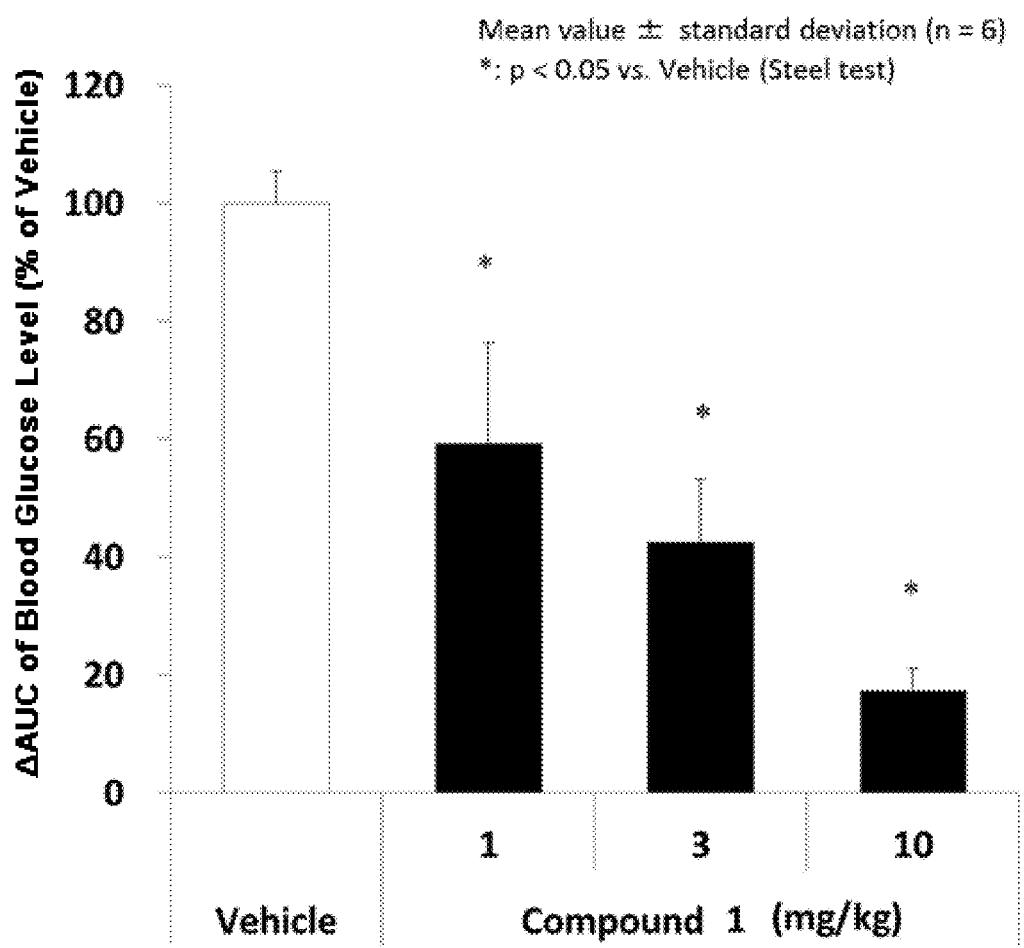

[Fig. 2]
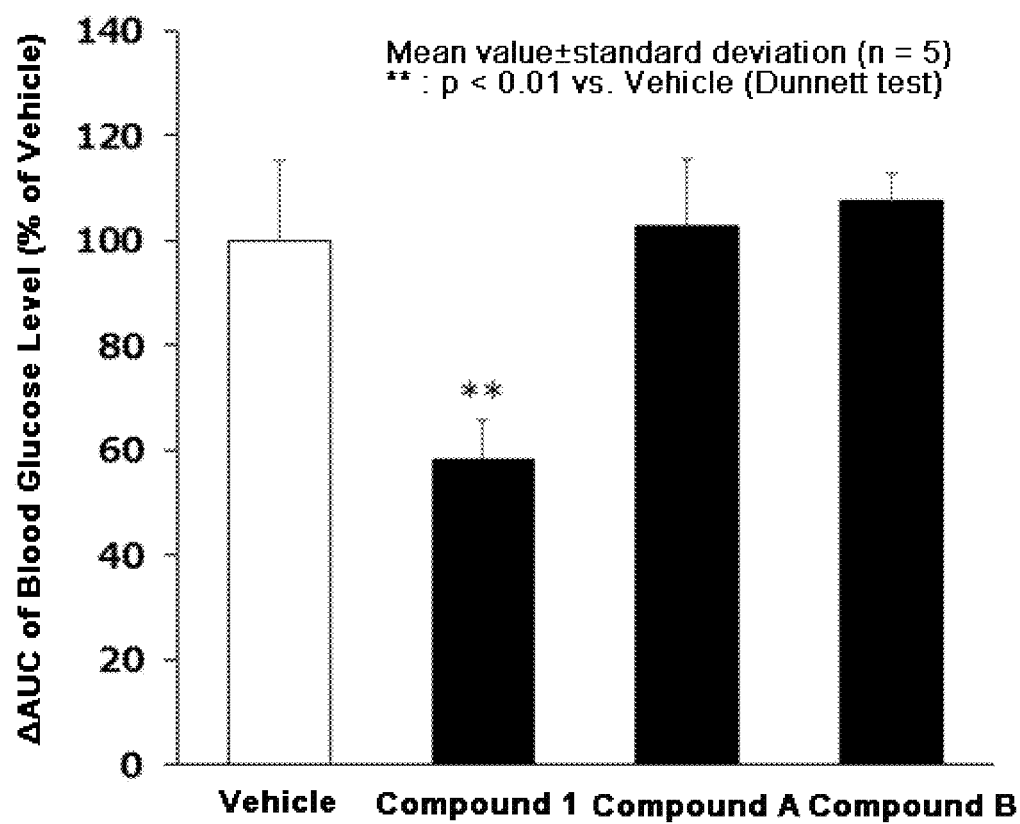

METHYLLACTAM RING COMPOUND AND PHARMACEUTICAL USE THEREOF

CROSS REFERENCE TO RELATED APPLICATIONS

This application claims priority to and benefit of Japanese Patent Application No. 2018-036307, filed Mar. 1, 2018, the disclosure of which is incorporated herein by reference in its entirety.

TECHNICAL FIELD

The present invention relates to a methyllactam ring compound having an SGLT1 inhibitory activity or a pharmaceutically acceptable salt thereof, a pharmaceutical composition comprising it, and pharmaceutical use thereof.

BACKGROUND ART

SGLT1, i.e., Sodium-Glucose Cotransporter 1, is known to contribute to a great portion of absorption of glucose and galactose in the small intestine. It is reported that human SGLT1-deficient patients cause glucose-galactose malabsorption. Furthermore, it is confirmed that the expression of SGLT1 in the small intestine increases in diabetic patients and it is thought that increased sugar absorption in diabetic patients is caused by the high expression of SGLT1 in the small intestine.

Based on the knowledge, an SGLT1 inhibitor is expected to normalize the blood glucose level by blocking glucose absorption in the small intestine. An SGLT1 inhibitor is, therefore, considered to be effective against diabetes and diabetic complications associated with hyperglycemia. It is also considered to be effective against obesity by inhibiting the inflow of glucose into the body (Non Patent Literatures 1 and 2).

Voglibose, a generic name, is a drug approved for manufacturing and marketing under the Japan Pharmaceutical Affairs Act Article 14 (Approval number: 21600AMZ00368). Voglibose improves excess blood glucose after eating by inhibiting disaccharidase, α-glucosidase, that degrades disaccharides existing in the intestinal mucosa into monosaccharides and inhibiting or delaying the digestion and absorption of carbohydrate in the intestinal tract. Such a pharmacological effect is known to be effective against delayed onset of type 2 diabetes in imparied glucose tolerance.

Based on the knowledge, inhibition of sugar absorption through small intestine with an SGLT1 inhibitor and thereby improvement of excess blood glucose after eating is thought to be effective against delayed onset of type 2 diabetes in imparied glucose tolerance.

The expression of SGLT1 is confirmed in cardiac muscle cells. It is known that GLUT1 (Glucose Transporter Type 1) and GLUT4 (Glucose Transporter Type 4) usually have a role in uptake of glucose into cardiac muscle cells and the contribution of SGLT1 is reduced. The expression of SGLT1 is, however, induced in the cardiac muscle of mice into which is introduced mutated genes of PRKAG2 (gamma 2 subunit of AMPK (AMP-Activated Protein Kinase)) which is a responsible gene of familial hypertrophic cardiomyopathy (glycogen accumulation-type myocardosis), or mice which undergo myocardial ischemia treatment, and SGLT1 is reported to contribute to the uptake of glucose to cardiac muscle cells in these pathologies. Glucose incorporated by SGLT1 is thought to be excessively accumulated or metabolized within cardiac muscle cells and impair the cells. It is reported in the former mouse model that accumulation of glycogen in the cardiac muscle is actually inhibited by the treatment of a non-selective SGLT inhibitor, phlorizin.

Based on the knowledge, an SGLT1 inhibitor is thought to be effective against hypertrophic cardiomyopathy and ischemic heart disease by inhibiting uptake of excess glucose into cardiac muscle cells (Non Patent Literatures 3 and 4).

SGLT1 is stabilized in cancer cells by epidermal growth factor receptors, i.e., surface proteins on many kinds of cancer cells. It is known that transporters of glucose, lactic acid, and amino acid, etc. are involved in nutrition supply to cancer cells, and especially, regarding the transportation of glucose, SGLT1 and GLUT1 continuously supply glucose to cancer cells. When glucose is not supplied over a long period of time, cells are destroyed by autophagy.

Based on the knowledge, an SGLT1 inhibitor is thought to inhibit supply of glucose to cancer cells and show anticancer activity (Non Patent Literatures 5 and 6).

Since carbohydrate is degraded to monosaccharides in the gastrointestinal tract in diet and is absorbed in the upper gastrointestinal tract, many sugars never reach the lower gastrointestinal tract. When, however, drugs that delay or inhibit glucose absorption are administered, or a large amount of resistant polysaccharides are ingested, then undigested sugars are retained in the lower gastrointestinal tract and the undigested sugars retained in the lower gastrointestinal tract cause osmotic diarrhea.

An SGLT1 inhibitor inhibits the glucose absorption and increases the amount of monosaccharides in the lower gastrointestinal tract. The SGLT1 inhibitor is, therefore, believed to be effective against constipation.

Diabetes is caused by elevated blood glucose level due to the deficient insulin action and the persistent elevated blood glucose may cause diabetic complication (e.g., retinopathy, nephropathy, and neuropathy, which are all known as microangiopathy; and cerebrovascular disease, ischemic heart disease, and membrum-inferius arteriosclerosis obliterans, which are all known as macroangiopathy). Other diseases associated with elevated blood glucose level include obesity.

Diabetes is classified as type 1 and type 2 diabetes. Type 1 diabetes is considered to be developed due to the deficient insulin action caused by destruction of pancreatic β cells that secretes insulin, whereas type 2 diabetes is considered to be developed due to environmental factors, such as overeating, insufficient exercise, obesity, and stress, and aging in addition to multiple genetic factors including a decrease in insulin secretion and insulin resistance. Diabetes is diagnosed using three types, such as the normal, borderline, and diabetic type, classified on the basis of the blood glucose level. When any one of the following (1) to (4):

(1) 126 mg/dL or more of blood glucose level in the morning fasting
(2) 200 mg/dL or more of two-hour value in 75 g OGTT (oral glucose tolerance test)
(3) 200 mg/dL or more of casual blood glucose level (4) 6.5% or more of HbA1cg
is identified, then the subject is determined as the diabetic type and diagnosed as diabetes or suspected diabetes (Non Patent Literature 7).

OGTT used in the above (2) is one of the methods for diagnosing diabetes. In general, when a human subject is administered a solution comprising 75 g of glucose after fasting, and a certain period of time after the administration of glucose, the blood glucose level is determined as 200 mg/dL or more, then the subject is diagnosed as diabetes (Non Patent Literature 7). OGTT is, therefore, an index of diabetes diagnosis, and a compound that can reduce blood glucose levels of glucose-loaded subjects in OGTT is considered to be effective against diabetes.

Non Patent Literatures

[Non Patent Literature 1] Am J Physiol Gastrointest Liver Physiol. 2002; 282(2):G241-8
[Non Patent Literature 2] Nature. 1991; 350(6316):354-6
[Non Patent Literature 3] J Mol Cell Cardiol. 2010; 49(4): 683-92
[Non Patent Literature 4] Cardiovasc Res. 2009; 84(1):111-8
[Non Patent Literature 5] Cancer Cell. 2008, 13: 385-93
[Non Patent Literature 6] Pharmacol Ther. 2009, 121: 29-40
[Non Patent Literature 7] Treatment Guide for Diabetes 2016-2017

SUMMARY OF INVENTION

A methyllactam ring compound that has an SGLT1 inhibitory activity and is useful for a drug, or a pharmaceutically acceptable salt thereof; a pharmaceutical composition comprising it; and pharmaceutical use thereof are provided.

After extensive studies, the present inventors found a specific methyllactam ring compound and achieved the present invention.

In one embodiment, a compound of Formula [I] or a pharmaceutically acceptable salt thereof, and pharmaceutical use thereof are provided.

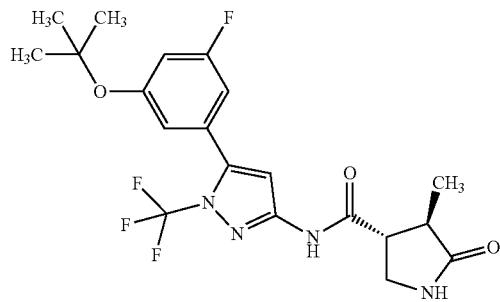

A compound of Formula [I] or a pharmaceutically acceptable salt thereof has an SGLT1 inhibitory activity and thus may be useful for the treatment and/or prevention of various diseases or conditions that can be expected to be improved by regulating the SGLT1 activity. A compound of Formula [I] or a pharmaceutically acceptable salt thereof may also be useful for the treatment and/or prevention of various diseases or conditions that can be caused by elevated blood glucose level.

BRIEF DESCRIPTION OF DRAWINGS

FIG. 1 shows that a compound of Example 1 (hereinafter, referred to as "Compound 1") significantly reduced the blood glucose level of glucose-loaded SD rats in OGTT in comparison with vehicle.

FIG. 2 shows that, among the test compounds, only Compound 1 significantly reduced the blood glucose level of glucose-loaded SD rats in OGTT in comparison with vehicle.

DESCRIPTION OF EMBODIMENTS

The present invention includes the embodiments illustrated as follows.

Item 1. A compound of Formula [I]:

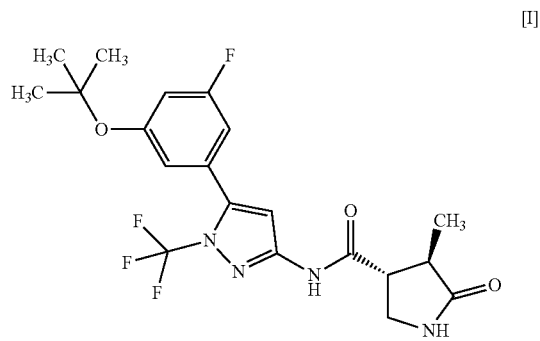 [SMILES: C[C@H]1C(=O)NC[C@@H]1C(=O)Nc1cc(-c2cc(F)cc(OC(C)(C)C)c2)n(C(F)(F)F)n1]

or a pharmaceutically acceptable salt thereof.

Item 2. A pharmaceutical composition comprising the compound according to Item 1 or a pharmaceutically acceptable salt thereof and a pharmaceutically acceptable carrier.

Item 3. An SGLT1 inhibitor comprising the compound according to Item 1 or a pharmaceutically acceptable salt thereof.

Item 4. A therapeutic or preventive agent for diabetes comprising the compound according to Item 1 or a pharmaceutically acceptable salt thereof.

Item 5. The therapeutic or preventive agent according to Item 4, wherein the diabetes is type 2 diabetes.

Item 6. A method for inhibiting SGLT1 comprising administering a therapeutically effective amount of the compound according to Item 1 or a pharmaceutically acceptable salt thereof to mammals.

Item 7. A method for treating or preventing diabetes comprising a therapeutically effective amount of the compound according to Item 1 or a pharmaceutically acceptable salt thereof to mammals.

Item 8. The method according to Item 7, wherein the diabetes is type 2 diabetes.

Item 9. Use of the compound according to Item 1 or a pharmaceutically acceptable salt thereof for the manufacture of an SGLT1 inhibitor.

Item 10. Use of the compound according to Item 1 or a pharmaceutically acceptable salt thereof for the manufacture of a therapeutic or preventive agent for diabetes.

Item 11. The use according to Item 10, wherein the diabetes is type 2 diabetes.

Item 12. A compound according to Item 1 or a pharmaceutically acceptable salt thereof for use in inhibiting SGLT1.

Item 13. A compound according to Item 1 or a pharmaceutically acceptable salt thereof for use in treating or preventing diabetes.

Item 14. The compound according to Item 13 or a pharmaceutically acceptable salt thereof, wherein the diabetes is type 2 diabetes.

Item 15. A commercial package comprising the composition according to Item 2 and a written matter associated therewith, the written matter indicating that the composition may or should be used for the treatment and/or prevention of diabetes.

Item 16. A kit comprising the composition according to Item 2 and a written matter associated therewith, the written matter indicating that the composition may or should be used for the treatment and/or prevention of diabetes.

The term "pharmaceutically acceptable salt" includes any salts known in the art that are not associated with excessive toxicity. Such a pharmaceutically acceptable salt includes, specifically, salts with inorganic acids, salts with organic acids, salts with inorganic bases, and salts with organic bases. Various forms of pharmaceutically acceptable salts are well known in the art and are described in, for example, the following references:
(a) Berge et al., J. Pharm. Sci., 66, p 1-19 (1977),
(b) Stahl et al., "Handbook of Pharmaceutical Sait: Properties, Selection, and Use" (Wiley-VCH, Weinheim, Germany, 2002),
(c) Paulekuhn et al., J. Med. Chem., 50, p 6665-6672 (2007).

A compound of Formula [I] may be reacted with an inorganic acid, organic acid, inorganic base, or organic base according to methods known per se to give a corresponding pharmaceutically acceptable salt thereof.

Such a salt with inorganic acid includes a salt with hydrofluoric acid, hydrochloric acid, hydrobromic acid, hydroiodic acid, nitric acid, phosphoric acid, and sulfuric acid. Such a salt preferably includes a salt with hydrochloric acid, nitric acid, sulfuric acid, phosphoric acid, and hydrobromic acid.

Such a salt with organic acid includes a salt with acetic acid, adipic acid, alginic acid, 4-aminosalicylic acid, anhydromethylenecitric acid, benzoic acid, benzenesulfonic acid, calcium edetate, camphor acid, camphor-10-sulfonic acid, carbonic acid, citric acid, edetic acid, ethane-1,2-disulfonic acid, dodecylsulfuric acid, ethanesulfonic acid, fumaric acid, glucoheptonic acid, gluconic acid, glucuronic acid, glucoheptonic acid, glycollylarsanilic acid, hexylresorcinol acid, hydroxynaphthoic acid, 2-hydroxy-1-ethanesulfonic acid, lactic acid, lactobionic acid, malic acid, maleic acid, mandelic acid, methanesulfonic acid, methylsulfuric acid, methylnitric acid, methylenebis(salicylic acid), galactaric acid, naphthalene-2-sulfonic acid, 2-naphthoic acid, 1,5-naphthalenedisulfonic acid, oleic acid, oxalic acid, pamoic acid, pantothenic acid, pectic acid, picric acid, propionic acid, polygalacturonic acid, salicylic acid, stearic acid, succinic acid, tannic acid, tartaric acid, teoclic acid, thiocyanic acid, trifluoroacetic acid, p-toluenesulfonic acid, undecanoic acid, aspartic acid, and glutamic acid. Such a salt preferably includes a salt with oxalic acid, maleic acid, citric acid, fumaric acid, lactic acid, malic acid, succinic acid, tartaric acid, acetic acid, trifluoroacetic acid, benzoic acid, glucuronic acid, oleic acid, pamoic acid, methanesulfonic acid, benzenesulfonic acid, p-toluenesulfonic acid, and 2-hydroxy-1-ethanesulfonic acid.

Such a salt with inorganic base includes a salt with lithium, sodium, potassium, magnesium, calcium, barium, aluminum, zinc, bismuth, and ammonium. Such a salt preferably includes a salt with sodium, potassium, calcium, magnesium, and zinc.

Such a salt with organic base includes a salt with arecoline, betaine, choline, clemizole, ethylenediamine, N-methylglucamine, N-benzylphenethylamine, tris(hydroxymethyl)methylamine, arginine, and lysine. Such a salt preferably includes a salt with tris(hydroxymethyl)methylamine, N-methylglucamine, and lysine.

A compound of Formula [I] or a pharmaceutically acceptable salt thereof may exist in its solvate form. The term "solvate" means a compound where a solvent molecule is coordinated with a compound of Formula [I] or a pharmaceutically acceptable salt thereof, and includes a hydrate. The solvate is preferably a pharmaceutically acceptable solvate; and includes, for example, a hydrate, an ethanolate, and a dimethyl sulfoxide solvate of a compound of Formula [I] or a pharmaceutically acceptable salt thereof. Such a solvate specifically includes hemihydrate, monohydrate, dihydrate, and monoethanolate of a compound of Formula [I]; and a monohydrate of sodium salt of a compound of Formula [I] and 2/3 ethanolate of dihydrochloride salt thereof. These solvates may be obtained according to any of the known methods.

A compound of Formula [I] may be labelled with an isotope such as $^2$H, $^3$H, $^{14}$C, and $^{35}$S.

A compound of Formula [I] or a pharmaceutically acceptable salt thereof is preferably a compound of Formula [I] or a pharmaceutically acceptable salt thereof that is substantively purified, and more preferably a compound of Formula [I] or a pharmaceutically acceptable salt thereof that has a purity of 80% or more.

A compound of Formula [I] or a pharmaceutically acceptable salt thereof has an SGLT1 inhibitory activity, and thus may be useful for the treatment and/or prevention of various diseases or conditions that can be expected to be improved by regulating the SGLT1 activity, for example, diabetes (e.g., type 1 diabetes and type 2 diabetes), obesity, diabetic complication (e.g., retinopathy, nephropathy, and neuropathy, which are all known as microangiopathy; and cerebrovascular disease, ischemic heart disease, and membrum-inferius arteriosclerosis obliterans, which are all known as macroangiopathy), hypertrophic cardiomyopathy, ischemic heart disease, cancer, and constipation.

The term "inhibiting SGLT1" means that the function of SGLT1 is inhibited so as to disappear or reduce its activity; and, for example, it means that the function of SGLT1 is inhibited on the basis of the following Test Example 1. The term "inhibiting SGLT1" means preferably "inhibiting human SGLT1". The inhibition of function, or the disappearance or reduction of activity is preferably carried out in human clinical indication.

The term "SGLT1 inhibitor" may be any substance that inhibits SGLT1, and includes small molecule compounds, nucleic acids, polypeptides, proteins, antibodies, and vaccines. The term "SGLT1 inhibitor" means preferably a "human SGLT1 inhibitor".

A compound of Formula [I] or a pharmaceutically acceptable salt thereof may also be useful for the treatment and/or prevention of various diseases or conditions that can be caused by elevated blood glucose level.

The term "various disease or conditions that can be caused by elevated blood glucose level" includes, for example, diabetes (e.g., type 1 diabetes and type 2 diabetes), obesity, and diabetic complication (e.g., retinopathy, nephropathy, and neuropathy, which are all known as microangiopathy; and cerebrovascular disease, ischemic heart disease, and membrum-inferius arteriosclerosis obliterans, which are all known as macroangiopathy).

The term "treatment" used herein includes the amelioration of conditions, prevention of aggravation, maintenance of remission, prevention of exacerbation, and prevention of relapse.

The term "prevention" used herein includes delaying the onset of conditions. For example, the "prevention of diabetes" includes delaying the onset of type 2 diabetes in imparied glucose tolerance.

A pharmaceutical composition herein may be prepared from a therapeutically effective amount of a compound of Formula [I] or a pharmaceutically acceptable salt thereof and at least one or more pharmaceutically acceptable carriers, optionally followed by mixing, according to methods known in the art of medicinal preparations. The amount of a compound of Formula [I] or a pharmaceutically acceptable salt thereof comprised in the pharmaceutical composition varies depending on a factor such as dosage forms and dosage amounts and ranges, for example, from 0.1 to 100% by weight of the total amount of the composition.

A dosage form to be formulated with a compound of Formula [I] or a pharmaceutically acceptable salt thereof includes oral preparations such as tablets, capsules, granules, powders, lozenges, syrups, emulsions, and suspensions; and parenteral preparations such as external preparations, suppositories, injections, eye drops, nasal preparations, and pulmonary preparations.

The term "pharmaceutically acceptable carrier" includes various organic or inorganic carrier substances which are conventionally used for a component of a formulation. Such substances include, for example, excipients, disintegrants, binders, fluidizers, and lubricants for solid preparations; solvents, solubilization agents, suspending agents, tonicity agents, buffering agents, and soothing agents for liquid preparations; and bases, emulsifying agents, wetting agents, stabilizers, stabilizing agents, dispersing agents, plasticizing agents, pH adjusters, absorption promoters, gelators, antiseptic agents, bulking agents, solubilizers, solubilization agents, and suspending agents for semisolid preparations. Additives such as preserving agents, antioxidant agents, coloring agents, and sweetening agents may be further added, if needed.

Such an "excipient" includes, for example, lactose, white soft sugar, D-mannitol, D-sorbitol, corn starch, dextrin, microcrystalline cellulose, crystalline cellulose, carmellose, carmellose calcium, sodium carboxymethylstarch, low-substituted hydroxypropylcellulose, and gum arabic.

Such a "disintegrant" includes, for example, carmellose, carmellose calcium, carmellose sodium, sodium carboxymethylstarch, croscarmellose sodium, crospovidone, low-substituted hydroxypropylcellulose, hydroxypropylmethyl cellulose, and crystalline cellulose.

Such a "binder" includes, for example, hydroxypropylcellulose, hydroxypropylmethyl cellulose, povidone, crystalline cellulose, white soft sugar, dextrin, starch, gelatin, carmellose sodium, and gum arabic.

Such a "fluidizer" includes, for example, light anhydrous silicic acid and magnesium stearate.

Such a "lubricant" includes, for example, magnesium stearate, calcium stearate, and talc.

Such a "solvent" includes, for example, purified water, ethanol, propylene glycol, macrogol, sesame oil, corn oil, and olive oil.

Such a "solubilization agent" includes, for example, propylene glycol, D-mannitol, benzyl benzoate, ethanol, triethanolamine, sodium carbonate, and sodium citrate.

Such a "suspending agent" includes, for example, benzalkonium chloride, carmellose, hydroxypropylcellulose, propylene glycol, povidone, methylcellulose, and glyceryl monostearate.

Such a "tonicity agent" includes, for example, glucose, D-sorbitol, sodium chloride, and D-mannitol.

Such a "buffering agent" includes, for example, disodium hydrogen phosphate, sodium acetate, sodium carbonate, and sodium citrate.

Such a "soothing agent" includes, for example, benzyl alcohol.

Such a "base" includes, for example, water, oils from animals or vegetables such as olive oil, corn oil, *arachis* oil, sesame oil, and castor oil, lower alcohols such as ethanol, propanol, propylene glycol, 1,3-butylene glycol, and phenol, higher fatty acids and esters thereof, waxes, higher alcohol, polyhydric alcohol, hydrocarbons such as white petrolatum, liquid paraffin, and paraffin, hydrophilic petrolatum, purified lanolin, absorption ointment, hydrous lanolin, hydrophilic ointment, starch, pullulan, gum arabic, tragacanth gum, gelatin, dextran, cellulose derivatives such as methylcellulose, carboxymethyl cellulose, hydroxyethyl cellulose, and hydroxypropyl cellulose, synthetic polymers such as carboxyvinyl polymer, sodium polyacrylate, polyvinylalcohol, and polyvinylpyrrolidone, propylene glycol, macrogol such as Macrogol 200 to 600, and a combination of two or more of them.

Such a "preserving agent" includes, for example, ethyl parahydroxybenzoate, chlorobutanol, benzyl alcohol, sodium dehydroacetate, and sorbic acid.

Such an "anti-oxidant agent" includes, for example, sodium sulfite and ascorbic acid.

Such a "coloring agent" includes, for example, food colors (e.g., Food Red No. 2 or No. 3, Food Yellow No. 4, or No. 5) and β-carotene.

Such a "sweetening agent" includes, for example, saccharin sodium, dipotassium glycyrrhizinate, and aspartame.

A pharmaceutical composition herein may be administered orally or parenterally (e.g., topically, rectally, intravenously, intramuscularly, and subcutaneously) to humans as well as mammals other than humans such as mice, rats, hamsters, guinea pigs, rabbits, cats, dogs, pigs, cows, horses, sheeps, and monkeys. The dosage amount varies depending on the subjects which will be administered to, diseases, conditions, dosage forms, and administration routes. For example, the daily dose for oral administration to an adult patient is typically within the range of about 0.01 mg to about 1 g of the active ingredient, i.e., a compound of Formula [I]. Such a dosage amount can be administered at one time or several times.

A kit such as kits for administration, treatment, and/or prevention, a package such as packaged goods, and a set and/or case of medicine which comprises a pharmaceutical composition comprising a compound of Formula [I] or a pharmaceutically acceptable salt thereof as the active ingredient or active agent and a written matter concerning the composition indicating that the composition may or should be used for treatment and/or prevention are also useful. Such a kit, package, and set of medicine may comprise one or more containers filled with the pharmaceutical composition or one or more active ingredients and other drugs or medicines (or ingredients) used for the composition. Examples of such a kit, package, and set of medicine include commercial kits, commercial packages, and commercial medicine set for appropriate use in the treatment and/or prevention of intended diseases. The written matter comprised in such a kit, package, and set of medicine includes a cautionary note or package insert in the form designated by the government organization that regulates manufactures, use, or sales of pharmaceutical or biological products which ensures an approval by the government organization on manufactures, use, or sales of products concerning administration to humans. The kit, package, and set of medicine may include packaged products as well as structures configured for appropriate administration steps and configured so as to be able to achieve more preferable medical treatment and/or prevention including treatment and/or prevention of intended diseases.

A method for preparing a compound of Formula [I] or a pharmaceutically acceptable salt thereof is illustrated as follows. A method for preparing a compound of Formula [I] or a pharmaceutically acceptable salt thereof is not limited thereto.

Each compound obtained in each step may be isolated and/or purified, if necessary, according to any of known methods such as distillation, recrystallization, and column chromatography, or optionally, a subsequent step can proceed without isolation and/or purification.

Herein, the term "room temperature" refers to a temperature which has not been controlled and includes 1° C. to 40° C. as one embodiment.

[Preparation Method A]

A compound of Formula [I] may be prepared according to Preparation Method A1 or A2 as shown in the following scheme. Preparation Method A1

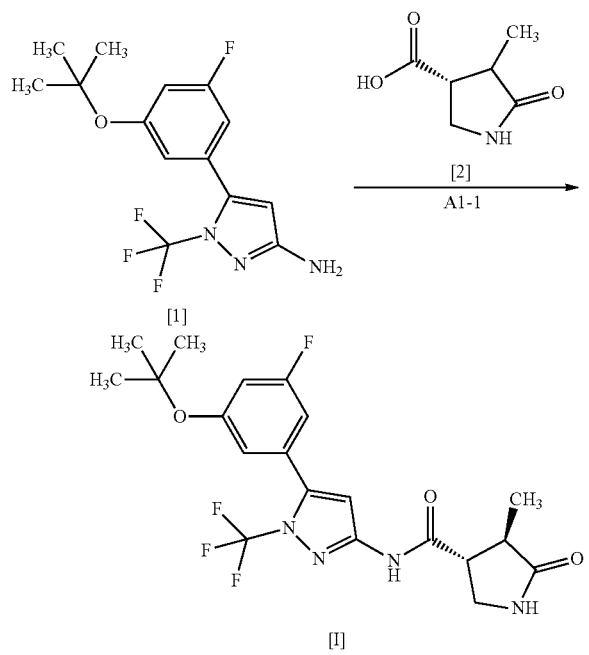

(Step A1-1)

A compound of Formula [I] may be prepared by reacting a compound of Formula [1] or a salt thereof with a compound of Formula [2] or a salt thereof in the presence of a condensation agent and additive in a solvent.

The condensation agent used herein includes, for example, dicyclohexylcarbodiimide (DCC), 1-ethyl-3-(3-dimethylaminopropyl)carbodiimide hydrochloride (WSC.HCl), diisopropylcarbodiimide, 1,1'-carbonyldiimidazole (CDI), O-(7-azabenzotriazol-1-yl)-N,N,N',N'-tetramethyluronium hexafluorophosphate (HATU), {{[(1-cyano-2-ethoxy-2-oxoethylidene)amino]oxy}-4-morpholinomethylene}dimethylammonium hexafluorophosphate (COMU), 4-(4,6-dimethoxy-1,3,5-triazin-2-yl)-4-methylmorpholinium chloride n-hydrate (DMT-MM), (benzotriazol-1-yloxy)tripyrrolidino phosphonium hexafluorophosphate (PyBOP), diphenylphosphoryl azide, and propylphosphonic acid anhydride.

The additive used herein includes, for example, 1-hydroxybenzotriazole (HOBt), 1-hydroxy-7-azabenzotriazole (HOAt), N-hydroxysuccinimide (HOSu), 4-dimethylaminopyridine, and 1-methylimidazole.

The solvent used herein includes, for example, halogenated hydrocarbon solvents such as chloroform; ether solvents such as tetrahydrofuran; polar solvents such as pyridine, acetonitrile, N,N-dimethylformamide; and a mixed solvent of any of these solvents.

The reaction temperature herein ranges, for example, from 0° C. to 100° C.

When a salt of a compound of Formula [1] is used, then the reaction may be carried out in the presence of a base. Such a base includes, for example, organic bases such as triethylamine and alkali metal salts such as sodium carbonate.

A compound of Formula [I] may also be prepared by converting a compound of Formula [2] with a halogenating agent into a corresponding carboxylic halide in a solvent, followed by reaction with a compound of Formula [1] in the presence of a base.

The halogenating agent used in the reaction includes, for example, oxalyl chloride and thionyl chloride. A preferable halogenating agent is oxalyl chloride.

The base used in the reaction includes, for example, organic bases such as pyridine, triethylamine, and N,N-diisopropylethylamine; and alkali metal salts such as sodium hydrogen carbonate and sodium carbonate. A preferable base is pyridine.

The solvent used herein includes, for example, halogenated hydrocarbon solvents such as chloroform; ether solvents such as cyclopentyl methyl ether and tetrahydrofuran; hydrocarbon solvents such as toluene; and a mixed solvent of any of these solvents with water. A preferable solvent is chloroform.

The reaction temperature herein ranges, for example, from 0° C. to 80° C., preferably from 0° C. to 60° C. In the preparation of carboxylic halide, N,N-dimethylformamide may be added as an additive.

Preparation Method A2

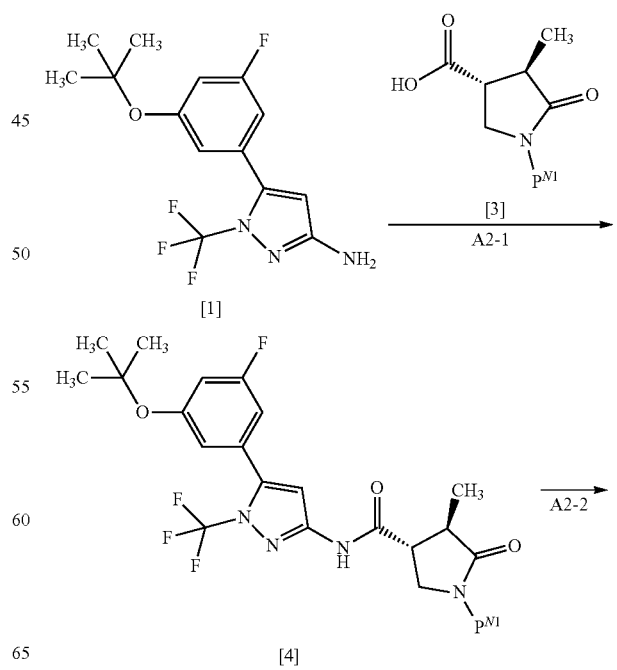

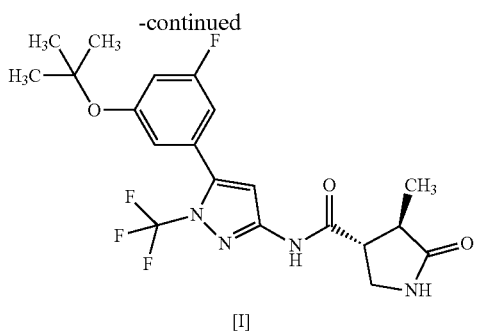

[I]

In the scheme, $P^{N1}$ is a protective group for amino group. $P^{N1}$ is preferably 2,4-dimethoxybenzyl group.

(Step A2-1)

A compound of Formula [1] or a salt thereof and a compound of Formula [3] or a salt thereof may be reacted according to Preparation Method A1 Step A1-1 to give a compound of Formula [4].

(Step A2-2)

A compound of Formula [I] or a salt thereof may be prepared by removing $P^{N1}$ from a compound of Formula [4] via a deprotection reaction. The deprotection reaction may be carried out under suitable conditions depending on $P^{N1}$.

For example, when $P^{N1}$ is 2,4-dimethoxybenzyl, a compound of Formula [I] or a salt thereof may be prepared by reaction with an acid in the presence of an additive in a solvent.

The acid used herein includes, for example, methanesulfonic acid, p-toluenesulfonic acid, and trifluoroacetic acid. A preferable acid is trifluoroacetic acid.

The additive used herein includes, for example, anisole and triethylsilane. A preferable additive is anisole.

The solvent used herein includes, for example, halogenated hydrocarbon solvents such as dichloromethane, hydrocarbon solvents such as toluene, water, and a mixed solvent of any of these solvents. An organic acid such as trifluoroacetic acid may also be used for the solvent.

The reaction temperature herein ranges, for example, from 0° C. to 130° C., preferably from 25° C. to 80° C.

When an acid is used in this step, a compound of Formula [5]:

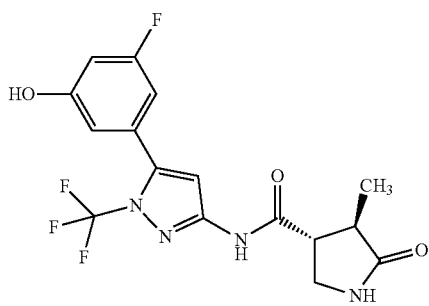

[5]

or a salt thereof is obtained. A compound of Formula [I] or a salt thereof may be prepared by converting hydroxyl group into tert-butoxy group in a compound of Formula [5] or a salt thereof according to any of known methods.

For example, a compound of Formula [I] or a salt thereof may be prepared by reacting a compound of Formula [5] or a salt thereof with di-tert-butyl dicarbonate in the presence of magnesium perchlorate.

The solvent used herein includes, for example, halogenated hydrocarbon solvents such as chloroform and ether solvents such as tetrahydrofuran. A preferable solvent is chloroform.

The reaction temperature herein ranges, for example, from 0° C. to 100° C., preferably from room temperature to 70° C.

[Preparation Method B]

A compound of Formula [1] may be prepared according to Preparation Method B1 as shown by the following scheme.

Preparation Method B1

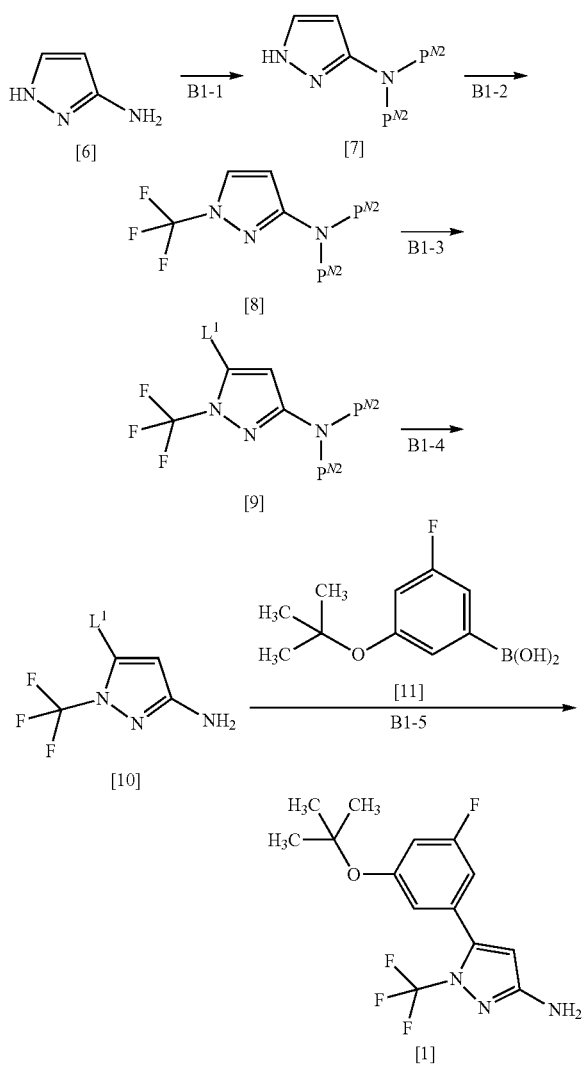

In the scheme, $L^1$ is a leaving group. $L^1$ is preferably chlorine, bromine, or iodine. $P^{N2}$ is each independently a protective group for amine. The two $P^{N2}$ are preferably combined with the nitrogen atom to which they are attached to form 2,5-dimethylpyrrole.

(Step B1-1)

A compound of Formula [7] or a salt thereof may be prepared by introducing $P^{N2}$ into the amino group in a compound of Formula [6] or a salt thereof according to any of known methods. The introduction of the protective group may be carried out under suitable conditions depending on $P^{N2}$. For example, when the two $P^{N2}$ are combined with the nitrogen atom to which they are attached to form 2,5-dimethylpyrrole, a compound of Formula [7] may be prepared by reacting a compound of Formula [6] with 2,5-hexanedione in a solvent under the acidic condition.

The acid used herein includes, for example, concentrated hydrochloric acid, concentrated sulfuric acid, amidosulfuric acid, p-toluenesulfonic acid, and acetic acid. A preferable acid is acetic acid.

The solvent used herein includes, for example, alcohol solvents such as ethanol, ether solvents such as tetrahydrofuran, hydrocarbon solvents such as toluene, polar solvents such as N,N-dimethylformamide, halogenated hydrocarbon solvents such as dichloroethane, and a mixed solvent of any of these solvents. An organic acid such as acetic acid may also be used for the solvent.

The reaction temperature herein ranges, for example, from room temperature to 150° C., preferably from 80° C. to 140° C.

(Step B1-2)

A compound of Formula [8] may be prepared by, for example, a process comprising:

Step (a): reacting a compound of Formula [7] with dibromodifluoromethane in the presence of a base and catalyst in a solvent, and Step (b): fluorinating the resultant in the presence of tetramethylammonium fluoride or silver (I) tetrafluoroborate in a solvent.

The base used in Step (a) includes, for example, sodium hydride and potassium tert-butoxide. A preferable base is sodium hydride.

The catalyst used in Step (a) includes, for example, tetrabutylammonium bromide and zinc. A preferable catalyst is tetrabutylammonium bromide.

The solvent used in Step (a) includes, for example, ether solvents such as tetrahydrofuran and polar solvents such as N,N-dimethylformamide. A preferable solvent is N,N-dimethylformamide.

The reaction temperature in Step (a) ranges, for example, from 0° C. to 40° C., preferably from 0° C. to room temperature.

When tetramethylammonium fluoride is used in Step (b), the solvent used therein includes, for example, ether solvents such as 1,4-dioxane and polar solvents such as sulfolane. A preferable solvent is sulfolane. When silver (I) tetrafluoroborate is used in Step (b), the solvent used therein includes, for example, halogenated hydrocarbon solvents such as dichloromethane. A preferable solvent is dichloromethane.

When tetramethylammonium fluoride is used in Step (b), the reaction temperature therein ranges, for example, from 80° C. to 180° C., preferably from 100° C. to 140° C. When silver (I) tetrafluoroborate is used in Step (b), the reaction temperature therein ranges, for example, from −78° C. to 50° C., preferably from −78° C. to room temperature.

(Step B1-3)

A compound of Formula [9] may be prepared by introducing $L^1$ into a compound of Formula [8] in the presence of a base in a solvent. For example, when $L^1$ is iodine, a compound of Formula [9] may be prepared by iodizing a compound of Formula [8] in the presence of a base in a solvent.

The base used herein includes, for example, n-butyllithium, lithium diisopropylamide, lithium hexamethyldisilazide, and lithium tetramethylpiperidide. A preferable base is n-butyllithium.

The iodizing agent used herein includes, for example, iodine, iodine monochloride, N-iodosuccinimide, and 1-chloro-2-iodoethane. A preferable iodizing agent is iodine.

The solvent used herein includes, for example, ether solvents such as tetrahydrofuran, hydrocarbon solvents such as toluene, and a mixed solvent of any of these solvents. A preferable solvent is tetrahydrofuran.

The reaction temperature herein ranges, for example, from −100° C. to 40° C., preferably from −78° C. to 20° C.

(Step B1-4)

A compound of Formula [10] or a salt thereof may be prepared by removing $P^{N2}$ from a compound of Formula [9] via a deprotection reaction. The deprotection reaction may be carried out under suitable conditions depending on $P^{N2}$. For example, when the two $P^{N2}$ are combined with the nitrogen atom to which they are attached to form 2,5-dimethylpyrrole, a compound of Formula [10] or a salt thereof may be prepared by reacting a compound of Formula [9] with hydroxylamine in a solvent.

The solvent used herein includes, for example, alcohol solvents such as ethanol, water, and a mixed solvent of any of these solvents. A preferable solvent is a mixed solvent of alcohol solvents with water.

The reaction temperature herein ranges, for example, from 40° C. to 150° C., preferably from 80° C. to 130° C.

Hydroxylamine hydrochloride may be used instead of hydroxylamine. In that case, the reaction may be carried out in the presence of a base. The base used herein includes, for example, organic bases such as triethylamine and alkali metal salts such as sodium carbonate. A preferable base is triethylamine.

(Step B1-5)

A compound of Formula [1] or a salt thereof may be prepared via Suzuki coupling reaction of a compound of Formula [10] or a salt thereof with a compound of Formula [11]. For example, a compound of Formula [1] or a salt thereof may be prepared by reacting a compound of Formula [10] or a salt thereof with a compound of Formula [11] in the presence of a base and palladium catalyst in a solvent.

The palladium catalyst used in the reaction includes, for example, tetrakis(triphenylphosphine)palladium, [1,1'-bis(diphenylphosphino)ferrocene]dichloropalladium (II)-dichloromethane adduct, [1,1'-bis(di-tert-butylphosphino)ferrocene]dichloropalladium (II), and a mixture of palladium (II) acetate and tricyclohexylphosphine, 2-dicyclohexylphosphino-2',6'-dimethoxybiphenyl, or 2-dicyclohexylphosphino-2',4',6'-triisopropylbiphenyl. A preferable palladium catalyst is [1,1'-bis(diphenylphosphino)ferrocene]dichloropalladium (II)-dichloromethane adduct.

The base used in the reaction includes, for example, tripotassium phosphate, cesium carbonate, sodium carbonate, sodium hydrogen carbonate, potassium carbonate, and triethylamine. A preferable base is tripotassium phosphate, cesium carbonate, or sodium carbonate.

The solvent herein includes, for example, ether solvents such as 1,4-dioxane, tetrahydrofuran, diethyl ether, and 1,2-dimethoxyethane; alcohol solvents such as methanol, ethanol, 1-propanol, and 2-propanol; hydrocarbon solvents such as toluene, n-hexane, and xylene; polar solvents such as N,N-dimethylformamide, dimethyl sulfoxide, and acetonitrile; and a mixed solvent of any of these solvents with water. A preferable solvent is 1,2-dimethoxyethane, toluene, dimethyl sulfoxide, or a mixed solvent of any of these solvents with water.

The reaction temperature herein ranges, for example, from 20° C. to 150° C., preferably from 80° C. to 130° C.

A compound of Formula [11] may be prepared according to any of known methods. A corresponding boronic acid ester may be used instead of a compound of Formula [11] in the reaction of step B1-5. For example, such a boronic acid ester may be prepared according to Preparation Method B2 as shown in the following scheme.

Preparation Method B2

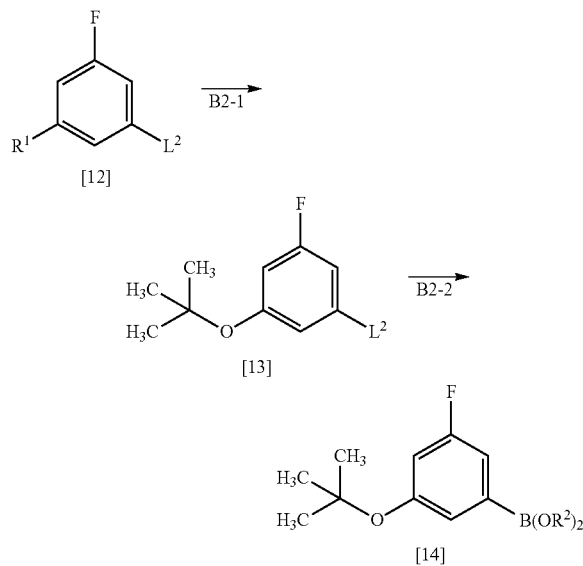

In the scheme, $R^1$ is fluorine or hydroxyl group. $L^2$ is a leaving group. $L^2$ is preferably chlorine, bromine, iodine, p-toluenesulfonyloxy, methanesulfonyloxy, or trifluoromethanesulfonyloxy. $B(OR^2)_2$ is boronic acid ester. $R^2$ is each independently, for example, methyl, ethyl, propyl, isopropyl, n-butyl, sec-butyl, or tert-butyl, or alternatively, $OR^2$ may be combined with boron to which they are attached to form a cyclic boronic acid ester. $B(OR^2)_2$ is preferably boronic acid pinacol ester.

(Step B2-1)

A compound of Formula [13] may be prepared by converting $R^1$ into tert-butoxy group in a compound of Formula [12]. The reaction may be carried out according to any of known methods.

When $R^1$ is fluorine, a compound of Formula [13] may be prepared by, for example, reacting a compound of Formula [12] with sodium tert-butoxide or potassium tert-butoxide in a solvent. The solvent used herein includes, for example, ether solvents such as tetrahydrofuran; and polar solvents such as N,N-dimethylformamide and dimethyl sulfoxide. A preferable solvent is N,N-dimethylformamide. The reaction temperature herein ranges, for example, from 0° C. to 100° C., preferably from room temperature to 85° C.

When $R^1$ is hydroxyl group, a compound of Formula [13] may be prepared according to, for example, the method for preparing a compound of Formula [I] or a salt thereof from a compound of Formula [5] or a salt thereof, as described in Preparation Method A2 Step A2-2.

(Step B2-2)

A compound of Formula [14] may be prepared by reacting a compound of Formula [13] with a boron compound in the presence of a palladium catalyst, organic phosphorus compound, and base in a solvent.

The palladium catalyst herein includes, for example, palladium (II) acetate, palladium (II) chloride, and tris(dibenzylideneacetone)dipalladium (0).

The organic phosphorus compound herein includes, for example, triphenylphosphine, tricyclohexylphosphine, 1,1'-bis(diphenylphosphino)ferrocene, 2-dicyclohexylphosphino-2',6'-dimethoxybiphenyl, 2-dicyclohexylphosphino-2',4',6'-triisopropylbiphenyl, and 2-dicyclohexylphosphino-2'-(N,N-dimethylamino)biphenyl.

Instead of the palladium catalyst and organic phosphorus compound, tetrakis(triphenylphosphine)palladium, [1,1'-bis(diphenylphosphino)ferrocene]dichloropalladium (II)-dichloromethane adduct, or [1,1'-bis(di-tert-butylphosphino)ferrocene]dichloropalladium (II) may be used.

The base herein includes, for example, potassium acetate, sodium carbonate, cesium carbonate, and potassium carbonate. A preferable base is potassium acetate.

The boron compound herein includes, for example, bis(pinacolato)diboron.

The solvent herein includes, for example, ether solvents such as 1,4-dioxane, tetrahydrofuran, and 1,2-dimethoxyethane; hydrocarbon solvents such as toluene; and polar solvents such as N,N-dimethylformamide and dimethyl sulfoxide. A preferable solvent is dimethyl sulfoxide.

The reaction temperature herein ranges, for example, from room temperature to 150° C., preferably from 70° C. to 110° C.

[Preparation Method C]

A compound of Formula [2] or a salt thereof and a compound of Formula [3] or a salt thereof may be prepared according to Preparation Method C1 as shown in the following scheme.

Preparation Method C1

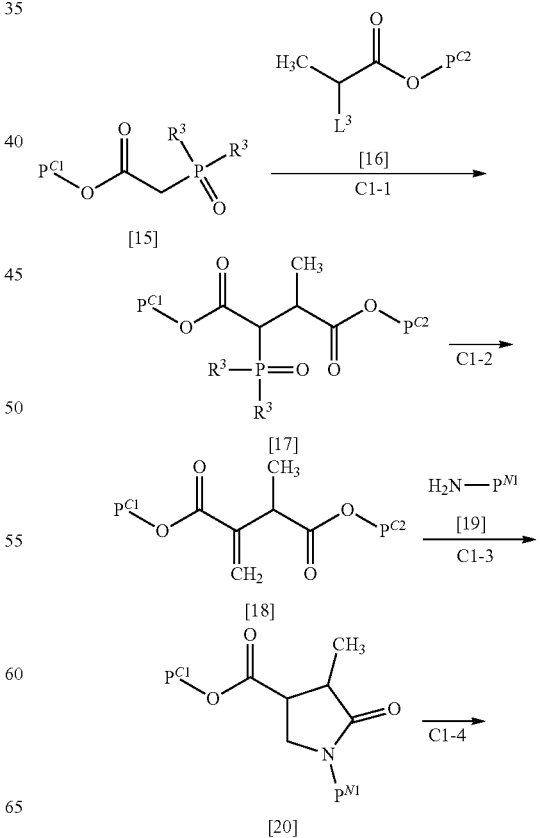

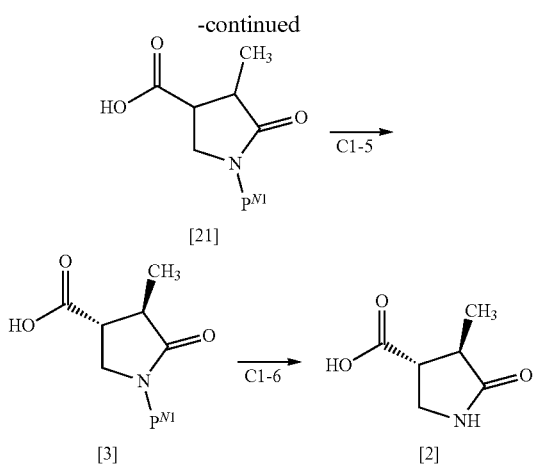

In the scheme, $P^{C1}$ and $P^{C2}$ are each independently a protective group for carboxy. Preferably, $P^{C1}$ and $P^{C2}$ are each independently methyl, ethyl, tert-butyl, or benzyl. $R^3$ is each independently methoxy or ethoxy. $L^3$ is a leaving group. $L^3$ is preferably bromine or chlorine. The other symbols have the same meanings each as described above.

(Step C1-1)

A compound of Formula [17] may be prepared by reacting a compound of Formula [15] with a compound of Formula [16] in the presence of a base in a solvent.

The base used in the reaction includes, for example, potassium tert-butoxide, sodium methoxide, sodium ethoxide, lithium diisopropylamide, potassium hexamethyldisilazane, potassium carbonate, cesium carbonate, and sodium hydride. A preferable base is potassium tert-butoxide.

The solvent herein includes, for example, ether solvents such as tetrahydrofuran; alcohol solvents such as methanol and ethanol; polar solvents such as N,N-dimethylformamide and dimethyl sulfoxide. A preferable solvent is tetrahydrofuran.

The reaction temperature herein ranges, for example, from −78° C. to 100° C., preferably from 0° C. to 70° C.

(Step C1-2)

A compound of Formula [18] may be prepared by reacting a compound of Formula [17] with formaldehyde (preferably, formaldehyde solution) in the presence of a base in a solvent.

The base used in the reaction includes, for example, potassium tert-butoxide, sodium methoxide, sodium ethoxide, lithium diisopropylamide, potassium hexamethyldisilazane, potassium carbonate, cesium carbonate, and sodium hydride. A preferable base is potassium carbonate.

The solvent herein includes, for example, ether solvents such as tetrahydrofuran; alcohol solvents such as methanol and ethanol; and polar solvents such as N,N-dimethylformamide and dimethyl sulfoxide. A preferable solvent is tetrahydrofuran.

The reaction temperature herein ranges, for example, from −78° C. to 100° C., preferably from 0° C. to 70° C.

(Step C1-3)

A compound of Formula [20] may be prepared by reacting a compound of Formula [18] with a compound of Formula [19] in a solvent.

The solvent herein includes, for example, hydrocarbon solvents such as toluene; alcohol solvents such as methanol and ethanol; and a mixed solvent of any of these solvents. A preferable solvent is toluene.

The reaction temperature herein ranges, for example, from 20° C. to 150° C., preferably from 80° C. to 130° C.

(Step C1-4)

A compound of Formula [21] or a salt thereof may be prepared by removing $P^{C1}$ from a compound of Formula [20] via a deprotection reaction. The deprotection reaction may be carried out under suitable conditions depending on $P^{C1}$. For example, when $P^{C1}$ is ethyl, a compound of Formula [21] or a salt thereof may be prepared by hydrolyzing a compound of Formula [20] in the presence of a base in a solvent.

The base used in the reaction includes, for example, lithium hydroxide, sodium hydroxide, potassium hydroxide, sodium ethoxide. A preferable base is sodium ethoxide.

The solvent herein includes, for example, alcohol solvents such as ethanol, ether solvents such as tetrahydrofuran, water, and a mixed solvent of any of these solvents. A preferable solvent is a mixed solvent of ethanol and water.

The reaction temperature herein ranges, for example, from 0° C. to 100° C., preferably from 0° C. to 40° C.

(Step C1-5)

A compound of Formula [3] or a salt thereof may be obtained by separation from a compound of Formula [21] or a salt thereof. The separation of a compound of Formula [3] or a salt thereof may be carried out under conditions suitable for the separation according to any of well-known methods in the art. For example, a compound of Formula [3] or a salt thereof may be obtained by separation of a diastereomer salt thereof with a basic optically resolving reagent, followed by treatment of the salt with an acid.

The basic optically resolving reagent herein includes, for example, (1R,2R)-(−)-2-amino-1-(4-nitrophenyl)-1,3-propanediol.

The solvent used in the introduction into the diastereomer salt includes, for example, alcohol solvents such as 2-propanol, ether solvents such as 1,2-dimethoxyethane, polar solvents such as acetonitrile, and a mixed solvent of any of these solvents with water. A preferable solvent is acetonitrile, 1,2-dimethoxyethane, or a mixed solvent of any of these solvents with water.

The optical purity of the diastereomer salt may be increased by recrystallization. The solvent used in the recrystallization includes, for example, ether solvents such as 1,2-dimethoxyethane, polar solvents such as acetonitrile, and a mixed solvent of any of these solvents with water. A preferable solvent is a mixed solvent of acetonitrile and water.

The acid used in the treatment of the diastereomer salt includes, for example, hydrochloric acid, sulfuric acid, and potassium hydrogen sulfate. A preferable acid is hydrochloric acid.

The solvent used in the treatment of the diastereomer salt includes, for example, ester solvents such as ethyl acetate, ether solvents such as tetrahydrofuran, water, and a mixed solvent of any of these solvents. A preferable solvent is a mixed solvent of ethyl acetate and water.

(Step C1-6)

A compound of Formula [2] or a salt thereof may be prepared by removing $P^{N1}$ from a compound of Formula [3] or a salt thereof via a deprotection reaction. The deprotection reaction may be carried out under suitable conditions depending on $P^{N1}$. For example, when $P^{N1}$ is 2,4-dimethoxybenzyl, a compound of Formula [2] or a salt thereof may be prepared according to Preparation Method A2 Step A2-2.

EXAMPLES

The present invention is illustrated in more detail with Preparations, Examples, Reference Examples, Test Examples, and Formulation Examples as below, but is not intended to be limited thereto.

The meanings of abbreviations used herein are shown as follows.

DMF: N,N-dimethylformamide
DMSO: dimethyl sulfoxide
THF: tetrahydrofuran
CPME: cyclopentyl methyl ether $^1$H-NMR spectra were measured in CDCl$_3$ or DMSO-d$_6$ with tetramethylsilane for internal standard substance, and all δ values are shown in ppm. The measurement was carried out with an NMR spectrometer with 400 MHz, unless otherwise specified.

Symbols in the Examples mean as follows.
s: singlet
d: doublet
t: triplet
q: quartet
dd: double doublet
ddd: double double doublet
brs: broad singlet
m: multiplet
J: coupling constant

[Preparation 1] Preparation of 2-(3-(tert-butoxy)-5-fluorophenyl)-4,4,5,5-tetramethyl-1,3,2-dioxaborolane

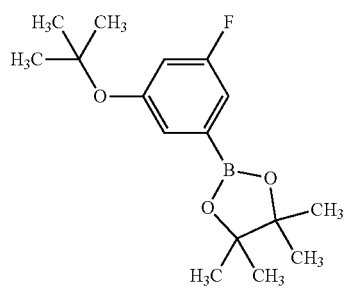 [SMILES: CC(C)(C)Oc1cc(F)cc(B2OC(C)(C)C(C)(C)O2)c1]

(Step 1) Preparation of 1-bromo-3-(tert-butoxy)-5-fluorobenzene

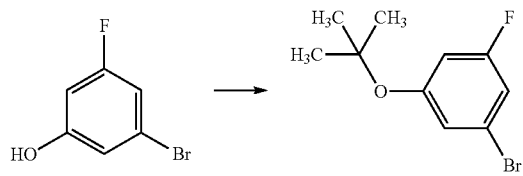

To 3-bromo-5-fluorophenol (500 mg) were sequentially added di-tert-butyl dicarbonate (1.14 g) and magnesium perchlorate (58 mg) at room temperature under argon flow. The reaction mixture was stirred at 50° C. for 1 hour 20 minutes. To the reaction mixture was added at 50° C. di-tert-butyl dicarbonate. The reaction mixture was stirred at 50° C. for 1 hour and further stirred at 65° C. for 1 hour, and then cooled to room temperature. To the reaction mixture was added at room temperature di-tert-butyl dicarbonate. The reaction mixture was stirred at 65° C. for 3 hours. The reaction mixture was cooled to room temperature, and thereto was added a mixed solution of n-hexane/ethyl acetate (1/1). The reaction mixture was sequentially washed with 3N hydrochloric acid, saturated aqueous sodium hydrogen carbonate solution, and brine, and then dried over sodium sulfate and concentrated. The residue was purified by silica gel column chromatography (eluent: n-hexane/ethyl acetate=1/0 to 20/1) to give the title compound (437 mg) in the yield of 68%.

$^1$H-NMR (CDCl$_3$) δ: 1.35 (s, 9H), 6.62-6.66 (m, 1H), 6.92-6.98 (m, 2H).

(Step 2) Preparation of 2-(3-(tert-butoxy)-5-fluorophenyl)-4,4,5,5-tetramethyl-1,3,2-dioxaborolane

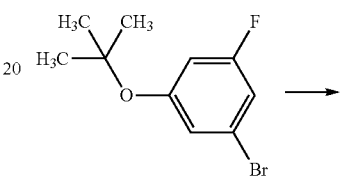

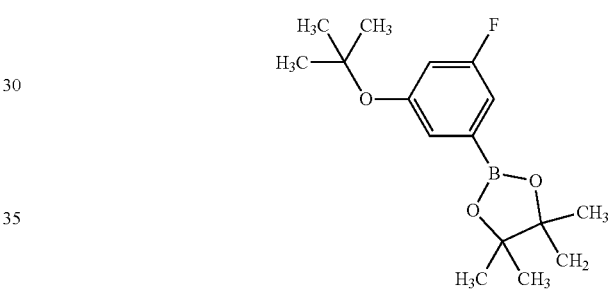

To a solution of 1-bromo-3-(tert-butoxy)-5-fluorobenzene (437 mg) obtained in Step 1 in DMSO (5 mL) were sequentially added potassium acetate (434 mg), bis(pinacolato)diboron (898 mg), and [1,1'-bis(diphenylphosphino)ferrocene]dichloropalladium (II)-dichloromethane adduct (144 mg) under argon atmosphere at room temperature. The reaction mixture was stirred at 90° C. for 2.5 hours. The reaction mixture was cooled to room temperature. To the reaction mixture were sequentially added a mixed solution of n-hexane/ethyl acetate (1/1) and water. The reaction mixture was stirred at room temperature for 50 minutes and let stand overnight. To the reaction mixture were sequentially added a mixed solution of n-hexane/ethyl acetate (1/1), water, silica gel, and celite. The reaction mixture was stirred, and then insoluble substances were filtered off and the insoluble substances were washed with a mixed solution of n-hexane/ethyl acetate (1/1). The filtrate was extracted with a mixed solution of n-hexane/ethyl acetate (1/1). The organic layer was sequentially washed with water twice and brine, dried over sodium sulfate, and concentrated. The residue was purified by silica gel thin-layer chromatography (eluent: n-hexane/ethyl acetate=10/1) to give the title compound (443 mg) in the yield of 85%.

$^1$H-NMR (CDCl$_3$) δ: 1.33 (s, 12H), 1.36 (s, 9H), 6.77-6.82 (m, 1H), 7.18-7.23 (m, 2H).

[Preparation 2] Preparation of (3R,4R)-1-(2,4-dimethoxybenzyl)-4-methyl-5-oxopyrrolidine-3-carboxylic acid

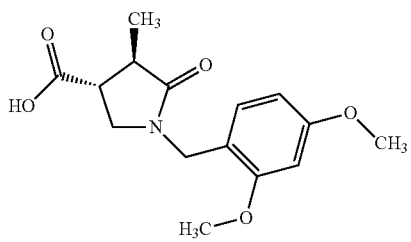 [SMILES: COc1ccc(CN2C[C@H](C(=O)O)[C@@H](C)C2=O)c(OC)c1]

(Step 1) Preparation of diethyl 2-methyl-3-methylenesuccinate

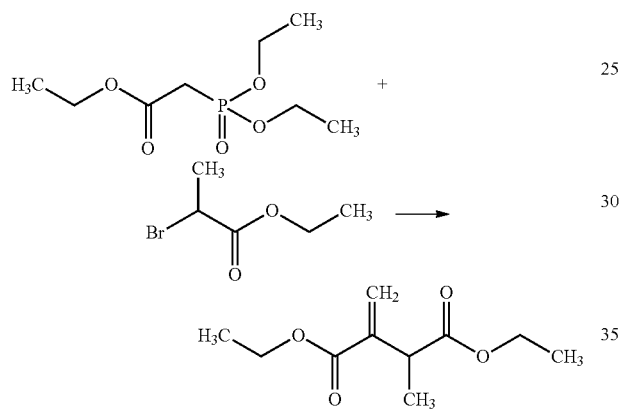

To potassium tert-butoxide (180 g) was added THF (2.55 L) at room temperature under nitrogen flow. To the mixture was added dropwise triethyl phosphonoacetate (314 g) under ice cooling over 13 minutes. The dropping funnel used was washed with THF (511 mL), and the washings were added to the reaction mixture. The reaction mixture was stirred for 2 hours 9 minutes under ice cooling. To the reaction mixture was added dropwise ethyl 2-bromopropionate (247 g) over 20 minutes under ice cooling. The dropping funnel used was washed with THF (79 mL), and the washings were added to the reaction mixture. The reaction mixture was stirred at room temperature for 22 hours 45 minutes. To the reaction mixture was added potassium carbonate (188 g) over 1 minute under ice cooling. To the reaction mixture was added dropwise 37% by weight of aqueous formaldehyde solution (152 mL) over 10 minutes under ice cooling. The reaction mixture was stirred at room temperature for 19 hours 44 minutes. To the reaction mixture was added water (1.57 L) at room temperature over 1 minute. The reaction mixture was stirred at room temperature for 1 hour 48 minutes. The reaction mixture was separated. The resulted aqueous layer was extracted with THF (200 mL) twice. The resulted organic layers were combined and concentrated. To the residue were added toluene (471 mL) and brine (471 mL). The reaction mixture was stirred and separated. The organic layer was dried over sodium sulfate (63 g). Sodium sulfate was filtered off. Separately, a similar reaction was performed with triethyl phosphonoacetate (300 g) to give a filtrate, which was then combined with the filtrate obtained above to give a solution of the title compound (equivalent to 2.66 mol) in toluene (about 921 mL). The resulted solution of the title compound in toluene was deemed to afford the yield of 100% and used in the next step. The generation of the title compound was confirmed by HPLC analysis.

The measuring instrument and conditions for HPLC are shown as follows.

Measuring instrument: HPLC system, Shimadzu Corporation, High-Performance Liquid Chromatograph Prominence
Measuring conditions:
Column: Kinetex C18: 2.6 μm, 50 mm×2.1 mm (Phenomenex)
Column temperature: 40° C.
Flow rate: 0.4 mL/min.
Time for analysis: 10 min.
Detection wavelength: UV (220 nm)
Mobile phase: (Solution A) water, (Solution B) acetonitrile
Delivery of mobile phase: A mixing ratio (Solution A/Solution B (volume %)) of Solution A and Solution B was maintained 80/20 from 0 minute to 0.01 minute after injection, changed linearly from 80/20 to 10/90 from 0.01 minute to 7 minutes, maintained 10/90 from 7 minutes to 8 minutes, changed linearly from 10/90 to 80/20 from 8 minutes to 9 minutes, and maintained 80/20 from 9 minutes to 10 minutes.

The retention time of the title compound was about 3.7 minutes under the measuring conditions for HPLC.

(Step 2) Preparation of a Mixture of ethyl (cis)-1-(2,4-dimethoxybenzyl)-4-methyl-5-oxopyrrolidine-3-carboxylate and ethyl (trans)-1-(2,4-dimethoxybenzyl)-4-methyl-5-oxopyrrolidine-3-carboxylate

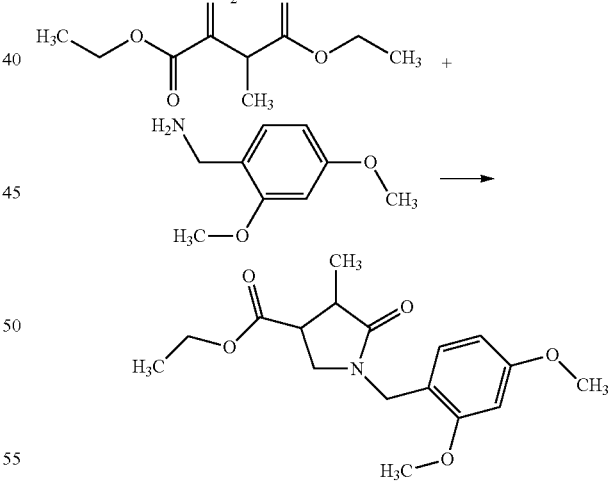

To a solution of diethyl 2-methyl-3-methylenesuccinate (equivalent to 2.66 mol) obtained in Step 1 in toluene (about 921 mL) was added dropwise 2,4-dimethoxybenzylamine (468 g) over 2 minutes at room temperature under nitrogen flow. The reaction mixture was stirred at 120° C. for 5 hours 45 minutes. The reaction mixture was let stand for a weekend at room temperature. The reaction mixture was cooled with ice to about 15° C. of the internal temperature. To the reaction mixture was added dropwise 2N hydrochloric acid (1.33 L), and the mixture was stirred. The reaction mixture was separated. The resulted aqueous layer was extracted with toluene (150 mL). The resulted organic layers were combined, washed with a mixed solution of brine and water (600 mL, brine/water=1/1), dried over sodium sulfate (120 g), concentrated, and dried under reduced pressure at room temperature overnight to give a crude product of the title compound (790 g; cis/trans=about 1/1, 5.5% by weight of toluene inclusive). The generation of the title compound was confirmed by HPLC analysis.

The measuring instrument and conditions for HPLC are shown as follows.
Measuring instrument: HPLC system, Shimadzu Corporation, High-Performance Liquid Chromatograph Prominence
Measuring conditions:
Column: Atlantis T3: 5 μm, 150 mm×4.6 mm (Waters)
Column temperature: 40° C.
Flow rate: 1.15 mL/min.
Time for analysis: 18 min.
Detection wavelength: UV (220 nm)
Mobile phase: (Solution A) 10 mM (sodium) phosphate buffer (pH=2.6), (Solution B) acetonitrile Delivery of Mobile phase: A mixing ratio (Solution A/Solution B (volume %)) of Solution A and Solution B was maintained 60/40 from 0 minute to 0.5 minute after injection, changed linearly from 60/40 to 10/90 from 0.5 minute to 8 minutes, maintained 10/90 from 8 minutes to 12.5 minutes, changed linearly from 10/90 to 60/40 from 12.5 minutes to 13.5 minutes, and maintained 60/40 from 13.5 minutes to 18 minutes.

The retention time was about 6.6 minutes for ethyl (cis)-1-(2,4-dimethoxybenzyl)-4-methyl-5-oxopyrrolidine-3-carboxylate and about 6.9 minutes for ethyl (trans)-1-(2,4-dimethoxybenzyl)-4-methyl-5-oxopyrrolidine-3-carboxylate under the measuring conditions for HPLC.

(Step 3) Preparation of (trans)-1-(2,4-dimethoxybenzyl)-4-methyl-5-oxopyrrolidine-3-carboxylic acid

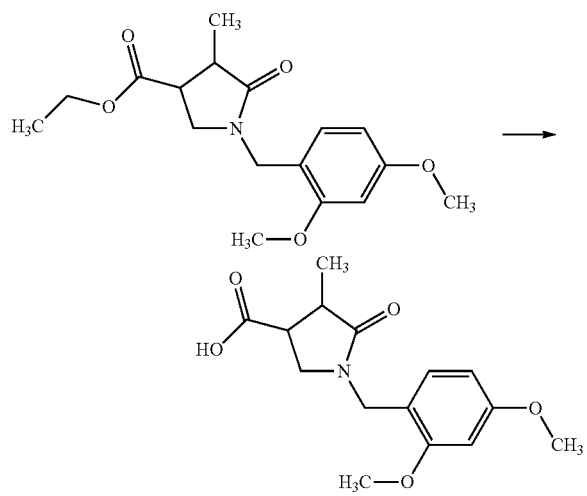

To a crude mixture (790 g, 5.5% by weight of toluene inclusive) of ethyl (cis)-1-(2,4-dimethoxybenzyl)-4-methyl-5-oxopyrrolidine-3-carboxylate and ethyl (trans)-1-(2,4-dimethoxybenzyl)-4-methyl-5-oxopyrrolidine-3-carboxylate, obtained in step 2, was added ethanol (1.15 L) at room temperature under nitrogen flow. To the reaction mixture was added dropwise sodium ethoxide (20% by weight solution in ethanol, 1.15 L) at room temperature over 31 minutes. The reaction mixture was stirred at room temperature for 2 hours 57 minutes. The reaction mixture was cooled with ice, and thereto was added dropwise water (1.84 L) over 33 minutes. To the reaction mixture were added CPME (1.8 L) and toluene (1.8 L) at room temperature, and the mixture was separated (Organic layer 1). To the resulted aqueous layer was added CPME (1.8 L), and the mixture was separated (Organic layer 2). Solvent (1.8 L) was removed from the resulted aqueous layer by evaporation. To the resulted aqueous layer was added dropwise 6N hydrochloric acid (110 mL) under ice cooling, and thereto was added ethyl acetate (1.8 L). To the mixture was added dropwise 6N hydrochloric acid (300 mL) under ice cooling, and the mixture was stirred for about 10 minutes. To the mixture were sequentially added water (2.2 L), 6N hydrochloric acid (50 mL), water (1.0 L), 10% by weight of aqueous sodium hydrogen sulfate solution (300 mL), and ethanol (300 mL) under ice cooling. The mixture was stirred at room temperature overnight. To the mixture was added ethyl acetate (600 mL), and the mixture was separated. The resulted aqueous layer was extracted with ethyl acetate (600 mL) twice. The resulted organic layers were combined (except for Organic layer 1 and Organic layer 2) and washed with a mixture of brine and water (1 L, brine/water=1/1). To the resulted organic layer were added sodium sulfate (120 g) and activated carbon (30 g), and the mixture was stirred at room temperature for 1 hour. The mixture was filtered through celite to remove insoluble substances. The insoluble substances were washed with ethyl acetate (3 L). The resulted filtrates were combined and concentrated, and dried under reduced pressure at room temperature for 3 hours to give a crude product of the title compound (561 g).

Separately, the above Organic layer 1 and Organic layer 2 were combined and concentrated. To the residue were added toluene (450 mL) and water (450 mL), and the mixture was separated. The resulted aqueous layer was washed with toluene (450 mL) twice. To the aqueous layer was added ethyl acetate (450 mL). To the mixture was added dropwise 6N hydrochloric acid (70 mL) under ice cooling. To the mixture was added ethyl acetate (300 mL), and the mixture was separated. The resulted aqueous layer was extracted with ethyl acetate (150 mL). The resulted organic layers of ethyl acetate were combined and washed with a mixture of brine and water (225 mL, brine/water=1/1). To the organic layer were added sodium sulfate (30 g) and activated carbon (7.5 g), and the mixture was stirred at room temperature for 1 hour. The mixture was filtered to remove insoluble substances. The insoluble substances were washed with ethyl acetate (750 mL). The resulted filtrates were combined and concentrated, and dried under reduced pressure at room temperature for 3 hours to give a crude product of the title compound (87.3 g).

This crude product was combined with the crude product of the title compound obtained above, and thereto was added CPME (3 L) under nitrogen flow. The mixture was stirred at 120° C. The mixture was slowly cooled to room temperature with stirring for 17 hours 34 minutes. The mixture was cooled with ice and stirred at about 1° C. of the internal temperature for 3 hours. The precipitate was filtered and washed with cooled CPME (900 mL). The precipitate was dried under reduced pressure at 50° C. overnight to give the title compound (585 g) in the total yield of 75% in the 3 steps. The generation of the title compound was confirmed by HPLC analysis and NMR.

The measuring instrument and conditions for HPLC are the same as those in Step 2. The retention time of the title compound was about 3.1 minutes under the measuring conditions for HPLC.

$^1$H-NMR (CDCl$_3$) δ: 1.33 (d, 3H, J=6.5 Hz), 2.68-2.85 (m, 2H), 3.33-3.48 (m, 2H), 3.80 (s, 6H), 4.43 (s, 2H), 6.42-6.46 (m, 2H), 7.11-7.15 (m, 1H).

(Step 4) Preparation of a Diastereomer Salt of (3R,4R)-1-(2,4-dimethoxybenzyl)-4-methyl-5-oxopyrrolidine-3-carboxylic acid with (1R,2R)-(−)-2-amino-1-(4-nitrophenyl)-1,3-propanediol

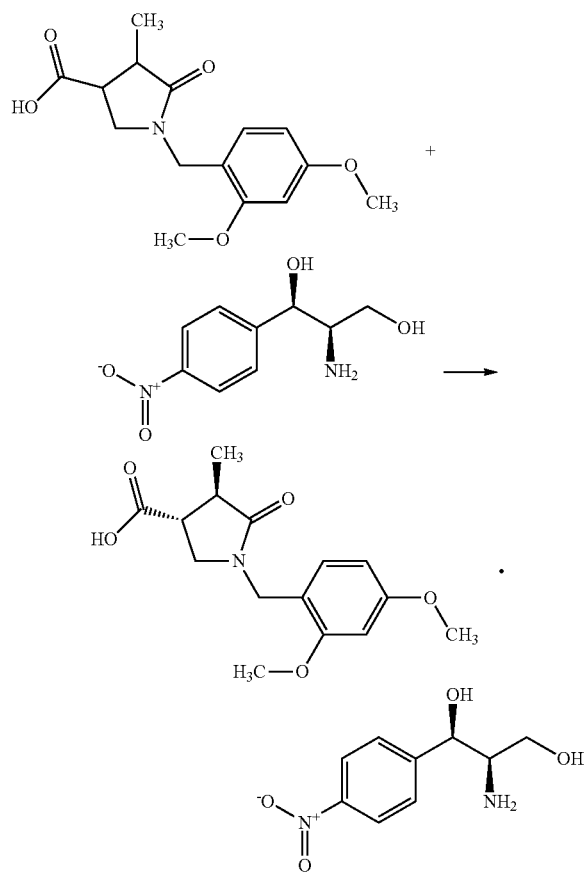

To (trans)-1-(2,4-dimethoxybenzyl)-4-methyl-5-oxopyrrolidine-3-carboxylic acid (585 g) obtained in Step 3 was added acetonitrile (2.9 L) at room temperature under nitrogen flow. The mixture was stirred at 85° C. To the mixture was added (1R,2R)-(−)-2-amino-1-(4-nitrophenyl)-1,3-propanediol (254 g) over 14 minutes at 85° C. The reaction mixture was stirred at 90° C. for 2 hours 48 minutes. The reaction mixture was cooled to room temperature with stirring overnight. The precipitate was filtered and washed with acetonitrile (2.4 L). The precipitate was dried under ordinary pressure for 8.5 hours at room temperature to give a crude crystal of the title compound (516 g). To the crude crystal were added acetonitrile (2.5 L) and water (0.5 L) at room temperature under nitrogen flow. The mixture was stirred at 100° C. for 1 hour 14 minutes. To the mixture was added dropwise acetonitrile (1.5 L) at 100° C. over 1 hour 7 minutes. The mixture was stirred at 100° C. for 10 minutes. The mixture was cooled to room temperature with stirring for 21 hours 10 minutes. The mixture was stirred for 3 hours 54 minutes under ice cooling. The precipitate was collected by filtration and washed with acetonitrile (1.5 L). The precipitate was dried under ordinary pressure at room temperature for 4 hours to give the title compound (448 g, 99.8% de) in the yield of 45%. The generation of the title compound was confirmed by HPLC analysis.

The measuring instrument and conditions for HPLC are shown as follows.

Measuring instrument: HPLC system, Shimadzu Corporation, High-Performance Liquid Chromatograph Prominence
Measuring conditions:
Column: CHIRAL PAK AD-3R: 3 µm, 150 mm×4.6 mm (Daicel)
Column temperature: 40° C.
Flow rate: 0.50 mL/min.
Time for analysis: 10 min.
Detection wavelength: UV (220 nm)
Mobile phase: (Solution A) 10 mM (sodium) phosphate buffer (pH=2.6), (Solution B) acetonitrile
Delivery of Mobile phase: A mixing ratio (Solution A/Solution B (volume %)) of Solution A and Solution B was maintained 60/40.

The retention time was about 5.6 minutes for (3R,4R)-1-(2,4-dimethoxybenzyl)-4-methyl-5-oxopyrrolidine-3-carboxylic acid and about 6.5 minutes for (3S,4S)-1-(2,4-dimethoxybenzyl)-4-methyl-5-oxopyrrolidine-3-carboxylic acid under the measuring conditions for HPLC.

The conformation of the title compound was determined by X-ray crystallography of its single crystal obtained after recrystallization from methyl isobutyl ketone.

Diastereomeric excess was determined from HPLC area percentages in the measurement results ((3R,4R)/(3S,4S) =99.886%/0.114%).

(Step 5) Preparation of (3R,4R)-1-(2,4-dimethoxybenzyl)-4-methyl-5-oxopyrrolidine-3-carboxylic acid

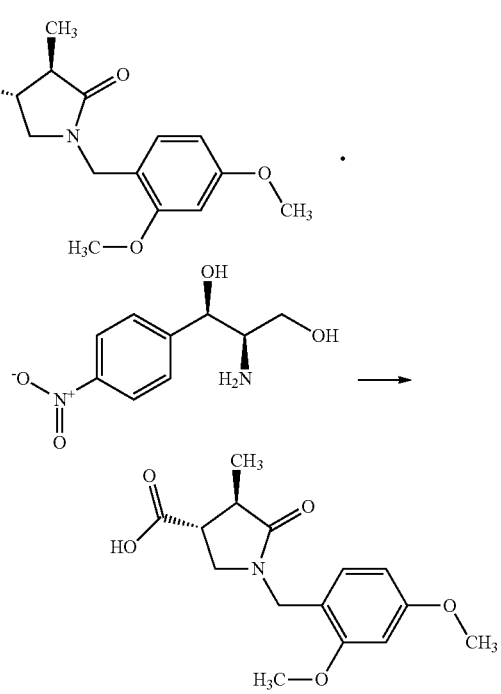

To a diastereomer salt of (3R,4R)-1-(2,4-dimethoxybenzyl)-4-methyl-5-oxopyrrolidine-3-carboxylic acid with (1R,2R)-(−)-2-amino-1-(4-nitrophenyl)-1,3-propanediol (448 g) obtained in Step 4 were added ethyl acetate (1.8 L) and water (1.34 L) at room temperature. To the mixture was added dropwise 6N hydrochloric acid (168 mL) at room temperature over 16 minutes. The mixture was separated. The resulted aqueous layer was extracted with ethyl acetate (450 mL) three times. The resulted organic layers were combined and washed sequentially with 2N hydrochloric acid (224 mL) and brine (224 mL), and then dried over sodium sulfate (90 g) and concentrated. To the residue was added toluene (220 mL), and the mixture was concentrated. The residue was dried under reduced pressure at room temperature to give the title compound (254 g) in the yield of 98%.

$^1$H-NMR (DMSO-$D_6$) δ: 1.15 (d, 3H, J=7.2 Hz), 2.50-2.58 (m, 1H), 2.73-2.83 (m, 1H), 3.18-3.25 (m, 1H), 3.30-3.38 (m, 1H), 3.75 (s, 3H), 3.77 (s, 3H), 4.19-4.35 (m, 2H), 6.48 (dd, 1H, J=8.4, 2.3 Hz), 6.56 (d, 1H, J=2.3 Hz), 7.00 (d, 1H, J=8.4 Hz), 12.61 (br s, 1H).

[Example 1] Synthesis of (3R,4R)—N-(5-(3-(tert-butoxy)-5-fluorophenyl)-1-(trifluoromethyl)-1H-pyrazol-3-yl)-4-methyl-5-oxopyrrolidine-3-carboxamide

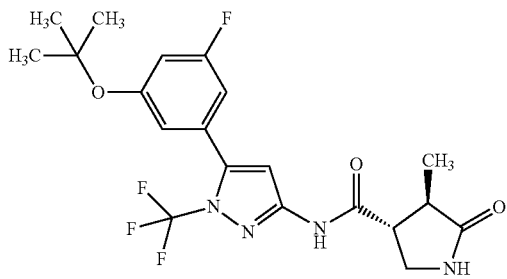 [SMILES: C[C@H]1C(=O)NC[C@@H]1C(=O)Nc1cc(-c2cc(F)cc(OC(C)(C)C)c2)n(C(F)(F)F)n1]

(Step 1) Preparation of 3-(2,5-dimethyl-1H-pyrrol-1-yl)-1H-pyrazole

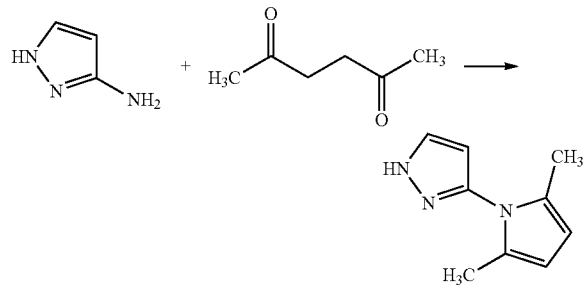

To 1H-pyrazol-3-amine (100 g) was added acetic acid (1 L) at room temperature, and the mixture was stirred for 5 minutes. To the mixture was added 2,5-hexanedione (148 mL) at room temperature, and the mixture was stirred for 5 minutes. The reaction mixture was stirred at 120° C. for 2.5 hours and cooled to room temperature. To the reaction mixture was added water (1 L) at room temperature. The reaction mixture was stirred at room temperature for 50 minutes. The precipitated solid was collected by filtration and washed with water (1 L). The resulted wet solid was dried under ordinary pressure at room temperature overnight, and then dried under reduced pressure at 65° C. for 3 days and 8.5 hours to give the title compound (172.47 g) in the yield of 89%.

$^1$H-NMR (CDCl$_3$) δ: 2.11 (s, 6H), 5.90 (s, 2H), 6.25 (d, 1H, J=2.4 Hz), 7.51 (d, 1H, J=2.4 Hz).

(Step 2) Preparation of a Mixture of 1-(bromodifluoromethyl)-3-(2,5-dimethyl-1H-pyrrol-1-yl)-1H-pyrazole and 1-(bromodifluoromethyl)-5-(2,5-dimethyl-1H-pyrrol-1-yl)-1H-pyrazole

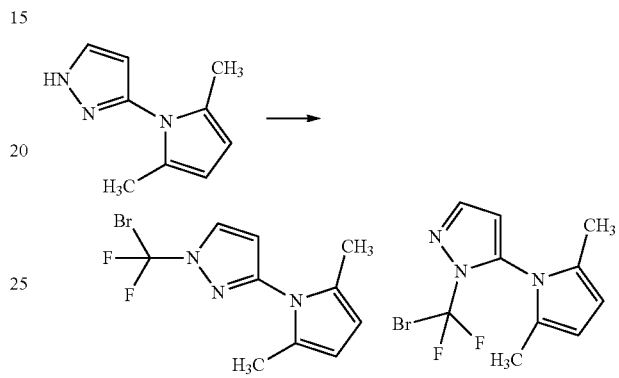

DMF (100 mL) was added to sodium hydride (14.9 g) under argon flow under ice cooling. To the mixture was added dropwise a suspension of 3-(2,5-dimethyl-1H-pyrrol-1-yl)-1H-pyrazole (40 g) obtained in Step 1 in DMF (150 mL) under ice cooling over 20 minutes. The dropping funnel used was washed with DMF (50 mL) and the washings were added to the reaction mixture. The reaction mixture was stirred under water cooling for 1.5 hours. To the reaction mixture was added tetrabutylammonium bromide (0.80 g) under ice cooling. The reaction mixture was stirred under ice cooling for 15 minutes. To the reaction mixture was added dropwise a solution of dibromodifluoromethane (45 mL) in DMF (50 mL) under ice cooling over 15 minutes. The reaction mixture was stirred under water cooling for 2 hours and 10 minutes. To the reaction mixture was added dropwise dibromodifluoromethane (20 mL) under argon atmosphere under water cooling. The reaction mixture was stirred under water cooling for 40 minutes, and then let stand overnight. To the reaction mixture was added saturated aqueous ammonium chloride solution (200 mL) under ice cooling. To the reaction mixture were added ethyl acetate and water. The reaction mixture was filtered through celite and the filtrate was separated. The resulted aqueous layer was extracted with ethyl acetate. The resulted organic layers were combined, and brine was added thereto. The mixture was filtered through celite and the filtrate was separated. The resulted aqueous layer was extracted with ethyl acetate. The resulted organic layers were combined, and then dried over sodium sulfate and concentrated. Toluene (250 mL) was added to the residue, and the mixture was concentrated. This procedure was repeated. Ethyl acetate (about 150 mL) was added to the residue, and the insoluble substances were filtered off. The insoluble substances were washed with ethyl acetate. The resulted filtrates were combined and concentrated. The residue was dried under reduced pressure with stirring at room temperature for 10 minutes. The residue was purified by silica gel column chromatography (eluent: n-hexane/ethyl acetate=30/1 to 20/1) to give the title compound (40.6 g, 3.7% by weight of hexane inclusive, 1-(bromodifluoromethyl)-3-(2,5-dimethyl-1H-pyrrol-1-yl)-1H-pyrazole:1-(bromodifluoromethyl)-5-(2,5-dimethyl-1H-pyrrol-1-yl)-1H-pyrazole=about 3:1) in the yield of 54%.

$^1$H-NMR (CDCl$_3$) δ: 2.03 (s, 1.5H), 2.18 (s, 4.5H), 5.89 (s, 1.5H), 5.91 (s, 0.5H), 6.39-6.41 (m, 1H), 7.86-7.88 (m, 1H).

(Step 3) Preparation of a Mixture of 3-(2,5-dimethyl-1H-pyrrol-1-yl)-1-(trifluoromethyl)-1H-pyrazole and 5-(2,5-dimethyl-1H-pyrrol-1-yl)-1-(trifluoromethyl)-1H-pyrazole

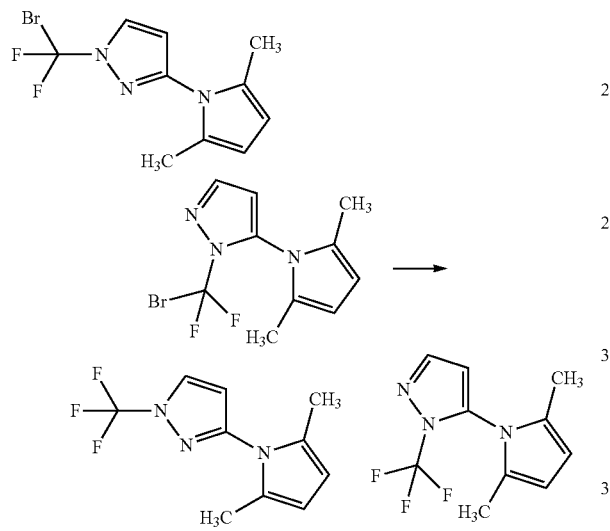

To a solution of a mixture of 1-(bromodifluoromethyl)-3-(2,5-dimethyl-1H-pyrrol-1-yl)-1H-pyrazole and 1-(bromodifluoromethyl)-5-(2,5-dimethyl-1H-pyrrol-1-yl)-1H-pyrazole (40.6 g, 3.7% by weight of hexane inclusive) obtained in Step 2 in sulfolane (400 mL) was added tetramethylammonium fluoride (13.0 g) at room temperature under argon flow. The reaction mixture was stirred at 100° C. for 1 hour. To the reaction mixture was added tetramethylammonium fluoride (9.4 g) at 100° C. The reaction mixture was stirred at 100° C. for 1 hour 15 minutes. To the reaction mixture was added tetramethylammonium fluoride (10 g) at 100° C. The reaction mixture was stirred at 100° C. for 40 minutes. In addition, to the reaction mixture was added tetramethylammonium fluoride (5 g) at 100° C. The reaction mixture was stirred at 100° C. for 2 hours 5 minutes, and then cooled to room temperature. To the reaction mixture were slowly and sequentially added water (400 mL) and saturated aqueous sodium hydrogen carbonate solution (200 mL) under ice cooling. To the reaction mixture was added a mixed solution of n-hexane/ethyl acetate (2/3) (400 mL). The reaction mixture was filtered through celite and the filtrate was separated. The resulted organic layer was washed with brine. The resulted aqueous layers were combined and extracted with a mixed solution of n-hexane/ethyl acetate (2/3) (300 mL). The organic layer was washed with brine. The resulted organic layers were combined, dried over sodium sulfate, and concentrated. The residue was purified by silica gel column chromatography (eluent: n-hexane/ethyl acetate=30/1 to 25/1) to give the title compound (21.85 g, 3-(2,5-dimethyl-1H-pyrrol-1-yl)-1-(trifluoromethyl)-1H-pyrazole:5-(2,5-dimethyl-1H-pyrrol-1-yl)-1-(trifluoromethyl)-1H-pyrazole=about 6:1, 24.4% by weight of n-hexane inclusive) in the yield of 51%.

$^1$H-NMR (CDCl$_3$) δ: 2.00 (s, 0.86H), 2.16 (s, 5.1H), 5.89 (s, 1.7H), 5.91 (s, 0.29H), 6.40 (d, 0.86H, J=2.8 Hz), 6.42 (d, 0.14H, J=1.6 Hz), 7.83 (d, 0.14H, J=1.6 Hz), 7.87 (d, 0.86H, J=2.8 Hz).

(Step 4) Preparation of 3-(2,5-dimethyl-1H-pyrrol-1-yl)-5-iodo-1-(trifluoromethyl)-1H-pyrazole

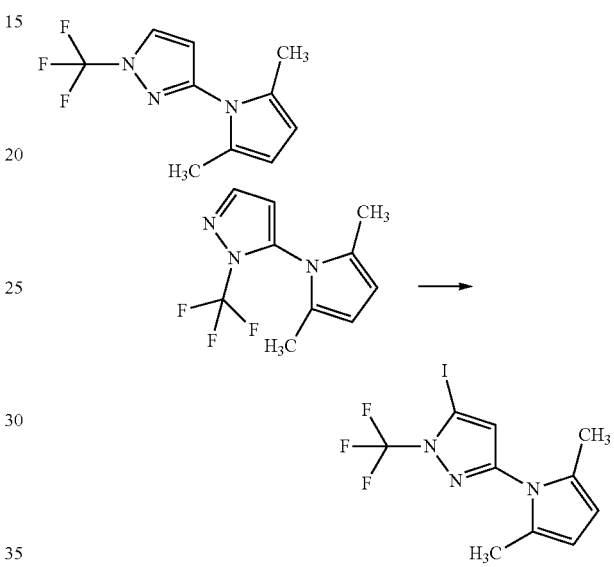

To a solution of a mixture of 3-(2,5-dimethyl-1H-pyrrol-1-yl)-1-(trifluoromethyl)-1H-pyrazole and 5-(2,5-dimethyl-1H-pyrrol-1-yl)-1-(trifluoromethyl)-1H-pyrazole (21.85 g, 24.4% by weight of n-hexane inclusive) obtained in Step 3 in THF (180 mL) was added dropwise a solution of n-butyllithium in n-hexane (1.55M, 51.1 mL) at −70° C. over 5 minutes under argon atmosphere. The reaction mixture was stirred at −70° C. for 25 minutes. To the reaction mixture was added dropwise a solution of iodine (18.3 g) in THF (50 mL) at −70° C. over 5 minutes. The dropping funnel used was washed with THF (10 mL), and the washings were added to the reaction mixture. The reaction mixture was stirred at −70° C. for 30 minutes. To the reaction mixture was added iodine (0.90 g) at −70° C. The reaction mixture was stirred at −70° C. for 0.5 hour. To the reaction mixture were sequentially added water (250 mL) and ethyl acetate (250 mL) at −70° C. The reaction mixture was stirred at room temperature and separated. The organic layer was sequentially washed with 10% by weight of aqueous sodium hydrogen sulfite solution (250 mL) and brine (150 mL), dried over sodium sulfate, and concentrated. The residue was purified by silica gel column chromatography (eluent: n-hexane/ethyl acetate=50/1 to 30/1). Fractions which include the title compound were collected and concentrated. To the residue was added n-hexane. The mixture was concentrated so that the weight of residue became 27.5 g. To the residue was added n-hexane (20 mL). The suspension was stirred at room temperature for 10 minutes. The precipitate was collected by filtration, washed with n-hexane (30 mL), and dried under reduced pressure to give the title compound (17.14 g) in the yield of 67%. Then, the filtrate was concentrated. The residue was crystallized from n-hexane to give the title compound (1.63 g) in the yield of 6.4%.

¹H-NMR (CDCl₃) δ: 2.15 (s, 6H), 5.88 (s, 2H), 6.60 (s, 1H).

(Step 5) Preparation of 5-iodo-1-(trifluoromethyl)-1H-pyrazol-3-amine

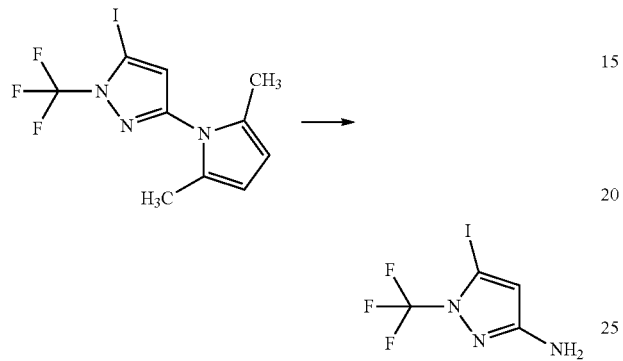

To 3-(2,5-dimethyl-1H-pyrrol-1-yl)-5-iodo-1-(trifluoromethyl)-1H-pyrazole (18.77 g) obtained in Step 4 were sequentially added a mixture of ethanol and water (ethanol/water=2/1, 480 mL), hydroxylamine hydrochloride (73.5 g), and triethylamine (14.7 mL) at room temperature. The reaction mixture was stirred at 100° C. for 38 hours 20 minutes. The reaction mixture was cooled to room temperature, and the ethanol was removed by evaporation. To the reaction mixture was slowly added a solution of sodium hydroxide (42.3 g) in water (130 mL), followed by addition of ethyl acetate (200 mL), under ice cooling. The reaction mixture was stirred, and separated. The resulted aqueous layer was extracted with ethyl acetate (200 mL). The resulted organic layers were combined, washed with brine, dried over sodium sulfate, and concentrated. To the residue were added ethyl acetate (30 mL) and n-hexane (30 mL), and insoluble substances were filtered off. The filtrate was concentrated. The residue was purified by silica gel column chromatography (eluent: n-hexane/ethyl acetate=4/1 to 3/1) to give the title compound (16.27 g, 14% by weight of ethyl acetate inclusive) in the yield of 96%.

¹H-NMR (CDCl₃) δ: 3.93 (br s, 2H), 6.09 (s, 1H).

(Step 6) Preparation of 5-(3-(tert-butoxy)-5-fluorophenyl)-1-(trifluoromethyl)-1H-pyrazol-3-amine

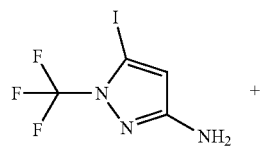

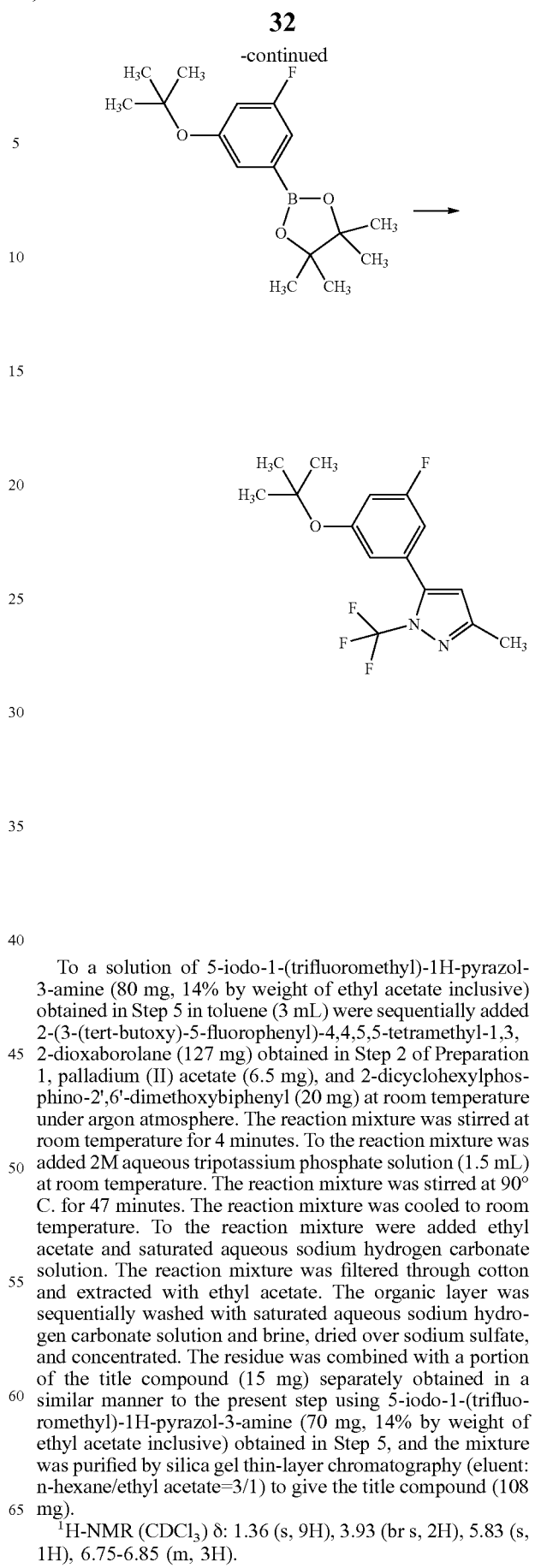

To a solution of 5-iodo-1-(trifluoromethyl)-1H-pyrazol-3-amine (80 mg, 14% by weight of ethyl acetate inclusive) obtained in Step 5 in toluene (3 mL) were sequentially added 2-(3-(tert-butoxy)-5-fluorophenyl)-4,4,5,5-tetramethyl-1,3,2-dioxaborolane (127 mg) obtained in Step 2 of Preparation 1, palladium (II) acetate (6.5 mg), and 2-dicyclohexylphosphino-2',6'-dimethoxybiphenyl (20 mg) at room temperature under argon atmosphere. The reaction mixture was stirred at room temperature for 4 minutes. To the reaction mixture was added 2M aqueous tripotassium phosphate solution (1.5 mL) at room temperature. The reaction mixture was stirred at 90° C. for 47 minutes. The reaction mixture was cooled to room temperature. To the reaction mixture were added ethyl acetate and saturated aqueous sodium hydrogen carbonate solution. The reaction mixture was filtered through cotton and extracted with ethyl acetate. The organic layer was sequentially washed with saturated aqueous sodium hydrogen carbonate solution and brine, dried over sodium sulfate, and concentrated. The residue was combined with a portion of the title compound (15 mg) separately obtained in a similar manner to the present step using 5-iodo-1-(trifluoromethyl)-1H-pyrazol-3-amine (70 mg, 14% by weight of ethyl acetate inclusive) obtained in Step 5, and the mixture was purified by silica gel thin-layer chromatography (eluent: n-hexane/ethyl acetate=3/1) to give the title compound (108 mg).

¹H-NMR (CDCl₃) δ: 1.36 (s, 9H), 3.93 (br s, 2H), 5.83 (s, 1H), 6.75-6.85 (m, 3H).

(Step 7) Preparation of (3R,4R)—N-(5-(3-(tert-butoxy)-5-fluorophenyl)-1-(trifluoromethyl)-1H-pyrazol-3-yl)-1-(2,4-dimethoxybenzyl)-4-methyl-5-oxopyrrolidine-3-carboxamide

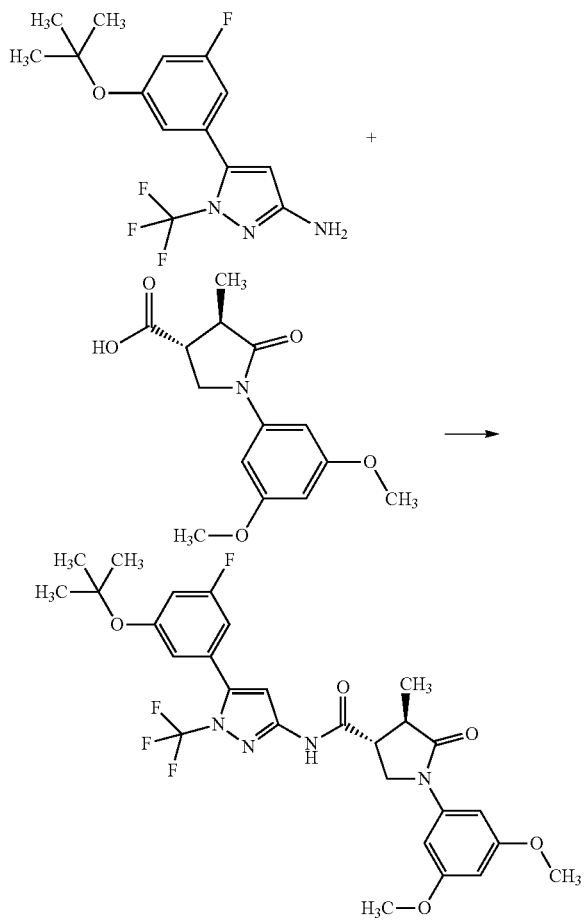

To a solution of (3R,4R)-1-(2,4-dimethoxybenzyl)-4-methyl-5-oxopyrrolidine-3-carboxylic acid (55 mg) obtained in a similar manner to Step 5 of Preparation 2 in chloroform (0.55 mL) were sequentially added DMF (1 μL) and oxalyl chloride (33 μL) under ice cooling under argon atmosphere. The reaction mixture was stirred under ice cooling for 50 minutes. The reaction mixture was concentrated and dried under reduced pressure. To the residue were sequentially added chloroform (0.4 mL) and 5-(3-(tert-butoxy)-5-fluorophenyl)-1-(trifluoromethyl)-1H-pyrazol-3-amine (40 mg) obtained in Step 6 under argon atmosphere under ice cooling. To the reaction mixture was added pyridine (50 μL) under ice cooling. The reaction mixture was stirred under ice cooling for 5 minutes and at room temperature for 35 minutes. To the reaction mixture was added saturated aqueous sodium hydrogen carbonate solution at room temperature, and the mixture was extracted with ethyl acetate. The organic layer was washed with brine, dried over sodium sulfate, and concentrated. The residue was purified by silica gel thin-layer chromatography (eluent: n-hexane/ethyl acetate=1/1) to give the title compound (60 mg) in the yield of 80%. The generation of the title compound was confirmed by thin-layer chromatography (eluent: n-hexane/ethyl acetate=2/1, Rf: 0.19).

(Step 8) Preparation of (3R,4R)—N-(5-(3-fluoro-5-hydroxyphenyl)-1-(trifluoromethyl)-1H-pyrazol-3-yl)-4-methyl-5-oxopyrrolidine-3-carboxamide

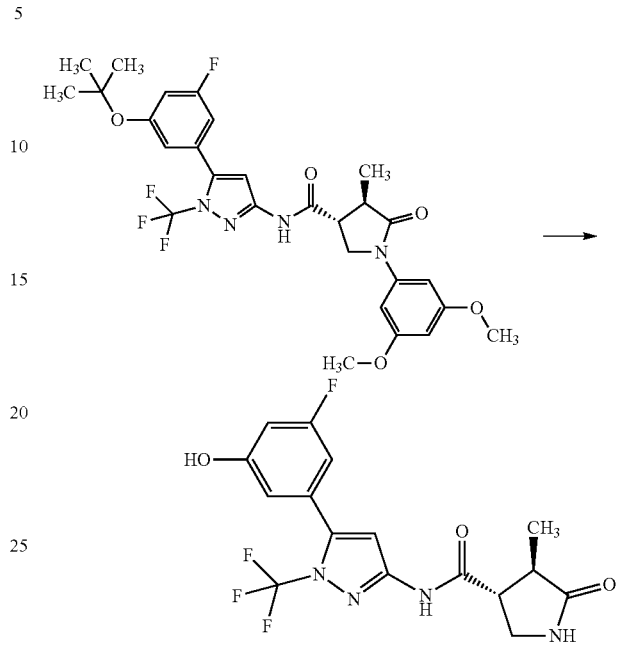

To (3R,4R)—N-(5-(3-(tert-butoxy)-5-fluorophenyl)-1-(trifluoromethyl)-1H-pyrazol-3-yl)-1-(2,4-dimethoxybenzyl)-4-methyl-5-oxopyrrolidine-3-carboxamide (60 mg) obtained in Step 7 were added anisole (58 μL) and trifluoroacetic acid (2 mL) at room temperature. The reaction mixture was stirred at 80° C. for 1 hour 20 minutes. The reaction mixture was concentrated. To the residue was added saturated aqueous sodium hydrogen carbonate solution, and the mixture was extracted with ethyl acetate. The organic layer was washed with brine, dried over sodium sulfate, and concentrated. The residue was purified by silica gel thin-layer chromatography (eluent: chloroform/ethyl acetate=1/1) to give the title compound (29.9 mg) in the yield of 76%.

$^1$H-NMR (DMSO-$d_6$) δ: 1.06 (d, 3H, J=7.2 Hz), 2.50-2.53 (m, 1H), 2.96-3.04 (m, 1H), 3.17-3.23 (m, 1H), 3.40-3.46 (m, 1H), 6.67-6.81 (m, 3H), 6.96 (s, 1H), 7.67 (s, 1H), 10.34 (s, 1H), 11.26 (s, 1H).

(Step 9) Preparation of (3R,4R)—N-(5-(3-(tert-butoxy)-5-fluorophenyl)-1-(trifluoromethyl)-1H-pyrazol-3-yl)-4-methyl-5-oxopyrrolidine-3-carboxamide

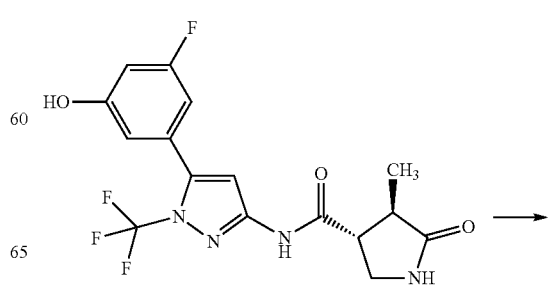

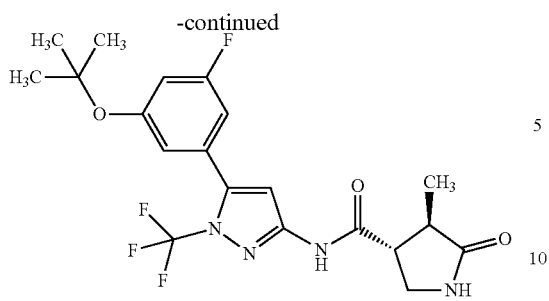

To (3R,4R)—N-(5-(3-fluoro-5-hydroxyphenyl)-1-(trifluoromethyl)-1H-pyrazol-3-yl)-4-methyl-5-oxopyrrolidine-3-carboxamide (30 mg) obtained in Step 8 were sequentially added di-tert-butyl dicarbonate, chloroform (1 mL) and magnesium perchlorate at room temperature. The reaction mixture was stirred at 55° C. for 0.5 hours. To the reaction mixture was added magnesium perchlorate at 55° C. The reaction mixture was stirred at 55° C. for 1 hour 10 minutes. To the reaction mixture was added the additional magnesium perchlorate at 55° C. The reaction mixture was stirred at 55° C. for 20 minutes. The reaction mixture was cooled to room temperature, and then thereto was added ethyl acetate. The reaction mixture was sequentially washed with 1N hydrochloric acid and brine, dried over sodium sulfate, and concentrated. The residue was purified by silica gel thin-layer chromatography (eluent: chloroform/methanol=15/1) to give the title compound (19.2 mg) in the yield of 56%.

$^1$H-NMR (DMSO-d$_6$) δ: 1.08 (d, 3H, J=7.2 Hz), 1.34 (s, 9H), 2.51-2.55 (m, 1H), 2.98-3.06 (m, 1H), 3.19-3.25 (m, 1H), 3.42-3.48 (m, 1H), 6.95 (s, 1H), 7.00-7.07 (m, 2H), 7.11-7.17 (m, 1H), 7.68 (s, 1H), 11.28 (s, 1H).

MS (M+H) 443, MS (M−H) 441.

(Step 10) Preparation of a Crystal of (3R,4R)—N-(5-(3-(tert-butoxy)-5-fluorophenyl)-1-(trifluoromethyl)-1H-pyrazol-3-yl)-4-methyl-5-oxopyrrolidine-3-carboxamide The title compound (100 mg) was stirred in ethanol (0.4 mL) at 65° C. for 8 minutes and dissolved. To the mixed solution was added dropwise water (0.4 mL) at 65° C. over 2 minutes. The mixture was stirred at 65° C. for 10 minutes. The mixture was cooled to 25° C. with stirring over 2 hours. Further, the mixture was stirred at room temperature for 2 hours. The solid precipitated from the mixture was collected by filtration. The obtained solid was washed with a mixed solution of ethanol/water (=1/1) and dried under reduced pressure at 60° C. to give a crystal of the title compound (87.8 mg) in the yield of 88%.

Reference Example

Compound A, Compound B, and Compound C, each of which is shown in the following table, were obtained according to the description of WO 2013/031922.

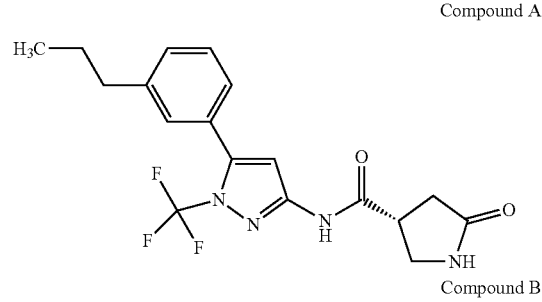

Compound A

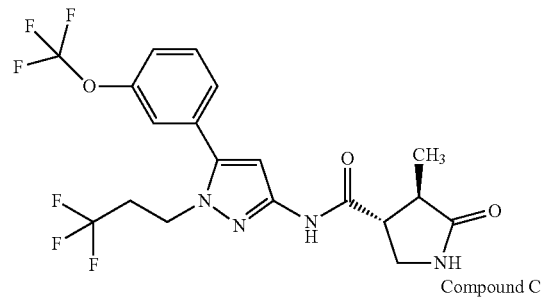

Compound B

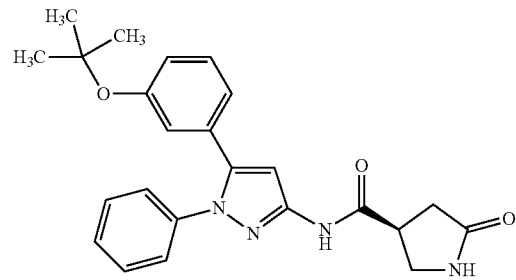

Compound C

Metabolite 1 (i.e., a metabolite of Compound 1) and Metabolite C (i.e., a metabolite of Compound C), each of which is shown in the following table, were obtained according to the above Example 1 and the description of WO 2013/031922.

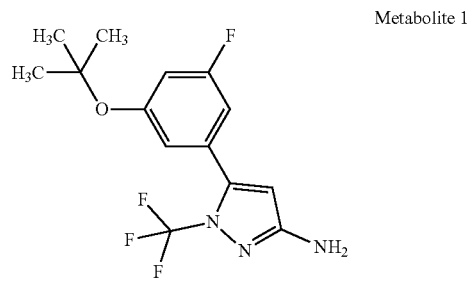

Metabolite 1

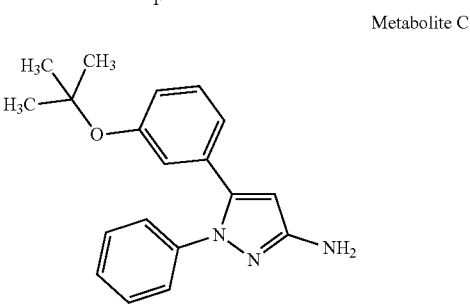

Metabolite C

Test Example 1

SGLT1 inhibitory activities of test compounds ($IC_{50}$ values) were calculated based on the amount of intracellular uptake of labelled α-methyl-D-glucopyranoside ($^{14}$C-AMG) transported by SGLT1.

1) Formation of Human SGLT1-Expressing Plasmid

A DNA fragment containing human SGLT1 was amplified by PCR (Polymerase Chain Reaction) using pCMV6-hSGLT1 (OriGene) as a template. In the human SGLT1, NheI recognition and cleavage sequence was added to the upstream of Kozac consensus sequence derived from a vector, and a stop codon, TAG, and SalI recognition and cleavage sequence were added to the immediate downstream of the protein-translating region of human SGLT1. The purified DNA fragment was cleaved by restriction enzymes NheI and SalI, followed by ligation with pcDNA3.1 (+) which was cleaved by NheI and XhoI, thereby forming human SGLT1-expressing plasmid. The nucleic acid sequence of human SGLT1 inserted into a vector was completely identical to the protein-translated region of human SGLT1 sequence (Accession number NM_000343) registered in GenBank, and the sequence of the portion connected to the vector was as expected.

2) Establishment of Human SGLT1-Stably-Expressing Cell Lines

Human SGLT-expressing plasmid, pcDNA-hSGLT1, was transfected into each CHO-K1 cell by Lipofectamine 2000 (Invitrogen) and cultured in the presence of G418 (Nacalai Tesque) to select drug-resistant cell lines. A cell line having the highest ratio (S/B ratio) of the amount of intracellular uptake of $^{14}$C-AMG per cell to the amount of intracellular uptake of $^{14}$C-AMG after treatment with a SGLT inhibitor, phlorizin, was selected as a human SGLT1-stably-expressing cell line from the drug-resistant cell lines.

3) Assessment of SGLT1 Inhibitory Activity

Human SGLT1-stably-expressing cell lines were seeded at 5×10$^4$ cells/well on BioCoat™ Poly-D-Lysine 96 well plate with Lid (Becton, Dickinson and Company) and cultured at 37° C. under 5% $CO_2$ overnight. The medium was replaced with 100 μL/well of Na(−) buffer (140 mM choline chloride, 2 mM KCl, 1 mM $MgCl_2$, 1 mM $CaCl_2$), 10 mM HEPES, 5 mM Tris, pH 7.4), and then the mixture was let stand at 37° C. under 5% $CO_2$ for 20 minutes. After removal of Na(−) buffer, thereto was added 40 μL/well of a test compound solution prepared with Na(+) buffer (140 mM NaCl, 2 mM KCl, 1 mM $MgCl_2$, 1 mM $CaCl_2$), 10 mM HEPES, 5 mM Tris, pH 7.4) comprising BSA. Then, thereto was added 40 μL/well of Na(+) buffer comprising 8 kBq of $^{14}$C-AMG and 2 mM AMG, and the mixture was mixed well. For a blank, 40 μL/well of Na(−) buffer comprising BSA was added, and in addition, 40 μL/well of Na(−) buffer comprising 8 kBq of $^{14}$C-AMG and 2 mM AMG was added, and the mixture was mixed well. After incubation by being let stand for 1 hour at 37° C. under 5% $CO_2$, cells were washed twice with 100 μL/well of ice-cooled wash buffer (100 mM AMG, 140 mM choline chloride, 2 mM KCl, 1 mM $MgCl_2$, 1 mM $CaCl_2$), 10 mM HEPES, 5 mM Tris, pH 7.4) to terminate the reaction. A cell lysate was prepared by addition of 50 μL/well of 0.2N aqueous NaOH solution. In the assessment for the uptake ability of $^{14}$C-AMG, the total amount of the cell lysate was transferred to OptiPlate 96 (Perkin-Elmer) with 100 μL/well of MicroScint-40 (Perkin-Elmer) dispensed and $^{14}$C of CPM was measured with TOPCOUNT NXT (Perkin-Elmer).

Data was calculated by deducting the average value of CPM for blank well from the average value of CPM for each well treated. An inhibition rate for each test compound in each concentration was calculated from the following equation:

$$[(A-B)/A]\times 100$$

wherein A is data for a solvent control and B is data for treatment with each test compound.

Each $IC_{50}$ value (50% inhibitory concentration) for each test compound was calculated based on two concentrations before and after a 50% inhibition rate and the inhibition rate. Compound 1 was confirmed to have the SGLT1 inhibitory activity in the assessment.

Test Example 2

OGTT (Oral Glucose Tolerance Test)

Vehicle (0.5% methylcellulose solution) or Compound 1 (1, 3, or 10 mg/kg) suspended in a 0.5% methylcellulose solution was orally administered in 5 mL/kg to an about 4-hour-fasted male SD rat (8-week old, Nihon Charles River K.K., 6 cases for each group). After 16 hours, glucose was loaded by oral administration of a 0.4 g/mL glucose solution in 5 mL/kg. Blood was collected from a tail vein just before the glucose load, and 30, 60 and 120 minutes after the glucose load; and the blood glucose level was measured with a biochemical automatic analyzer (HITACHI, Model No. 7180).

The results are shown in FIG. 1. Data shows mean values±standard deviation of the ratio of the area under the curve (Δ AUC) for blood glucose levels from the glucose load to 120 minutes of the compound-administered groups to that of the vehicle group (% of Vehicle). Statistical analyses were based on Steel's multiple test. The significance level was two-sided 5%. The results show that Compound 1 significantly reduced the blood glucose level after the glucose load compared to vehicle.

Test Example 3

OGTT (Oral Glucose Tolerance Test)

Vehicle (0.5% methylcellulose solution) or Compound 1, Compound A, or Compound B (3 mg/kg each) suspended in a 0.5% methylcellulose solution was orally administered in 5 mL/kg to an about 4-hour-fasted male SD rat (8-week old, Nihon Charles River K.K., 5 cases for each group). After 16 hours, glucose was loaded by oral administration of a 0.4 g/mL glucose solution in 5 mL/kg. Blood was collected from a tail vein just before the glucose load, and 30, 60 and 120 minutes after the glucose load; and the blood glucose level was measured with a biochemical automatic analyzer (HITACHI, Model No. 7180).

The results are shown in FIG. 2. Data shows mean values±standard deviation of the ratio of the area under the curve (Δ AUC) for blood glucose levels from the glucose load to 120 minutes of the compound-administered groups to that of the vehicle group (% of Vehicle). Statistical analyses were based on Dunnett's multiple group test. The significance level was two-sided 5%. The results show that only Compound 1 significantly reduced the blood glucose level after the glucose load compared to vehicle.

Test Example 4

Ames Test (Reverse Mutation Test)

Metabolite 1 and Metabolite C were each tested herein. The purpose of this test is to evaluate the potential of each metabolite to induce reverse mutations in the standard strains of *Salmonella typhimurium* (TA98, TA1537, TA100, and TA1535) and *Escherichia coli* (WP2uvrA), in either the presence or absence of a rat liver metabolic activation system (S9 mix).

The solvent used herein was dimethyl sulfoxide (DMSO, 100 μL/plate).

The test was performed by the pre-incubation method with or without S9 mix. When the test was performed without S9 mix, sodium phosphate buffer solution (pH 7.4) was added.

0.5 mL of S9 mix or 0.5 mL of 0.1 mol/L sodium phosphate buffer solution (pH 7.4), and 0.1 mL of the bacterial culture solution were added to a test tube containing 0.1 mL of the negative control formulation (DMSO alone), the metabolite, or the positive control formulation. The mixtures were pre-incubated at 37° C. for 20 minutes while shaking. After the pre-incubation period, 2 mL of top agar were added and the mixtures were vortex-mixed and seeded onto plates. Two plates per treatment were used. Each plate was incubated at 37±1° C. for 48 hours or more and the revertant colonies were counted. The mean number of revertant colonies for each treatment plate was then calculated. The presence or absence of growth inhibition due to any antibacterial effect of the test article and precipitation of the test article was observed grossly or under a stereomicroscope. The results were judged as positive if the mean number of revertant colonies showed a dose dependent increase which reached 2-fold over that of the negative control at one or more doses. Evaluation was based on mean values with no statistical comparisons being used.

The results of the test are shown in the following tables (Tables 1 to 4 and Tables 5 to 7). In conclusion, Metabolite 1 did not have potential to induce reverse mutations in any of the bacterial tester strains, whereas Metabolite C had potential to induce reverse mutations in the bacterial tester strains of TA98 with S9 mix and TA100 with S9 mix.

The number of revertant colonies shows the mean number of each plate.

TABLE 2

| Test article | Dose (μg/plate) | S9 Mix | Number of revertant colonies | | |
|---|---|---|---|---|---|
| | | | TA1537 | TA1535 | WP2uvrA |
| DMSO | (0.1 mL) | + | 13 | 12 | 25 |
| Metabolite 1 | 2.3 | + | 11 | 13 | 31 |
| | 6.9 | + | 10 | 7 | 31 |
| | 21 | + | 9 | 6 | 32 |
| | 62 | + | 6 | 8 | 40 |
| | 185 | + | 2 * | 5 * | 16 * |
| | 556 | + | 0 * | 4 * | 18 * |
| | 1667 | + | 0 * | 4 * | 9 * |
| | 5000 † | + | 0 * | 2 * | 0 * |
| 2AA | 2.0 | + | — | 223 | — |
| | 10.0 | + | — | — | 818 |
| B[a]P | 5.0 | + | 119 | — | — |

+: Presence of S9 mix
\* Growth inhibition
†: Precipitation
—: Not tested
DMSO: Dimethyl sulfoxide
2AA: 2-Aminoanthracene
B[a]P: Benzo[a]pyrene The number of revertant colonies shows the mean number of each plate.

TABLE 1

| Test article | Dose (μg/plate) | S9 Mix | Number of revertant colonies | |
|---|---|---|---|---|
| | | | TA98 | TA100 |
| DMSO | (0.1 mL) | + | 36 | 133 |
| Metabolite 1 | 2.3 | + | 35 | 120 |
| | 6.9 | + | 31 | 119 |
| | 21 | + | 35 | 117 |
| | 62 | + | 28 | 104 |
| | 185 | + | 16 * | 78 * |
| | 556 † | + | 15 * | 59 * |
| | 1667 † | + | 13 * | 50 * |
| | 5000 † | + | 13 * | 52 * |
| B[a]P | 5.0 | + | 455 | 1069 |

+: Presence of S9 mix
\* Growth inhibition
†: Precipitation
DMSO: Dimethyl sulfoxide
B[a]P: Benzo[a]pyrene

TABLE 3

| Test article | Dose (μg/plate) | S9 Mix | Number of revertant colonies WP2uvrA |
|---|---|---|---|
| DMSO | (0.1 mL) | + | 31 |
| Metabolite 1 | 6.9 | + | 31 |
| | 12 | + | 28 |
| | 21 | + | 25 |
| | 36 | + | 34 |
| | 62 | + | 35 |
| | 107 | + | 25 |
| | 185 | + | 9 * |
| 2AA | 10.0 | + | 740 |

+: Presence of S9 mix
\*: Growth inhibition
DMSO: Dimethyl sulfoxide
2AA: 2-Aminoanthracene The number of revertant colonies shows the mean number of each plate.

TABLE 4

| Test article | Dose (μg/plate) | S9 Mix | Number of revertant colonies | | | | |
|---|---|---|---|---|---|---|---|
| | | | TA98 | TA1537 | TA100 | TA1535 | WP2uvrA |
| DMSO | (0.1 mL) | − | 18 | 8 | 100 | 8 | 26 |
| Metabolite 1 | 2.3 | − | 14 | 7 | 99 | 6 | 32 |
| | 6.9 | − | 16 | 10 | 113 | 9 | 27 |
| | 21 | − | 14 | 9 | 124 | 8 | 31 |
| | 62 | − | 21 | 9 | 88 | 8 | 24 |

TABLE 4-continued

| Test article | Dose (μg/plate) | S9 Mix | Number of revertant colonies | | | | |
|---|---|---|---|---|---|---|---|
| | | | TA98 | TA1537 | TA100 | TA1535 | WP2uvrA |
| | 185 | − | 9 * | 0 * | 38 * | 0 * | 15 * |
| | 556 | − | 0 * | 0 * | 0 * | 0 * | 8 * |
| | 1667 | − | 0 * | 0 * | 0 * | 0 * | 5 * |
| | 5000 † | − | 0 * | 0 * | 0 * | 0 * | 0 * |
| AF-2 | 0.01 | − | — | — | 633 | — | 69 |
| | 0.1 | − | 341 | — | — | — | — |
| ICR-191 | 1.0 | − | — | 1170 | — | — | — |
| SA | 0.5 | − | — | — | — | 217 | — |

—: Note tested
* Growth inhibition
†: Precipitation
DMSO: Dimethyl sulfoxide
AF-2: 2-(2-Furyl)-3-(5-nitro-2-furyl)acrylamide
SA: Sodium azide
ICR-191: 2-Methoxy-6-chloro-9-[3-(2-chloroethyl)-aminopropylamino]acridine dihydrochloride The number of revertant colonies shows the mean number of each plate.

TABLE 5

| Test article | Dose (μg/plate) | S9 Mix | Number of revertant colonies | |
|---|---|---|---|---|
| | | | TA98 | TA100 |
| DMSO | (0.1 mL) | + | 28 | 117 |
| Metabolite C | 2.34 | + | 38 | 526 # |
| | 4.69 | + | 36 | 778 # |
| | 9.38 | + | 73 # | 1210 # |
| | 18.8 | + | 107 # | 1745 # |
| | 37.5 | + | 133 # | 2049 # |
| | 75 | + | 153 # | 2147 # |
| | 150 | + | 133 # | 2043 # |
| | 300 | + | 138 * | 1412 * |
| B[a]P | 5.0 | + | 404 | 1078 |

: The results were judged as positive if the mean number of revertant colonies showed a dose dependent increase which reached 2-fold over that of the negative control.
* Growth inhibition
DMSO: Dimethyl sulfoxide
B[a]P: Benzo[a]pyrene The number of revertant colonies shows the mean number of each plate.

TABLE 6

| Test article | Dose (μg/plate) | | S9 Mix | Number of revertant colonies | | |
|---|---|---|---|---|---|---|
| | | | | TA1537 | TA1535 | WP2uvrA |
| DMSO | (0.1 mL) | | + | 6 | 5 | 21 |
| Metabolite C | 2.3 | | + | 6 | 8 | 28 |
| | 6.9 | | + | 7 | 8 | 23 |
| | 21 | | + | 7 | 5 | 21 |
| | 62 | | + | 9 * | 4 * | 26 |
| | 185 | | + | 9 * | 5 * | 17 |
| | 556 | † | + | 4 * | 4 * | 8 * |
| | 1667 | † | + | 4 * | 5 * | 12 * |
| | 5000 | † | + | 5 * | 4 * | 16 * |
| 2AA | 2.0 | | + | — | 250 | — |
| | 10.0 | | + | — | — | 685 |
| B[a]P | 5.0 | | + | 80 | — | — |

—: Not tested
* Growth inhibition
†: Precipitation
DMSO: Dimethyl sulfoxide
2AA: 2-Aminoanthracene
B[a]P: Benzo[a]pyrene The number of revertant colonies shows the mean number of each plate.

TABLE 7

| Test article | Dose (μg/plate) | | S9 Mix | Number of revertant colonies | | | | |
|---|---|---|---|---|---|---|---|---|
| | | | | TA98 | TA1537 | TA100 | TA1535 | WP2uvrA |
| DMSO | (0.1 mL) | | − | 17 | 6 | 86 | 6 | 18 |
| Metabolite C | 2.3 | | − | 14 | 3 | 87 | 6 | 15 |
| | 6.9 | | − | 15 | 1 * | 99 | 5 * | 16 |
| | 21 | | − | 17 | 3 * | 48 * | 6 * | 17 |
| | 62 | | − | 8 | 3 * | 41 * | 3 * | 13 |
| | 185 | | − | 8 * | 2 * | 45 * | 4 * | 13 |
| | 556 | † | − | 8 * | 0 * | 33 * | 0 * | 13 * |
| | 1667 | † | − | 8 * | 0 * | 25 * | 1 * | 10 * |
| | 5000 | † | − | 0 * | 0 * | 35 * | 0 * | 11 * |
| AF-2 | 0.01 | | − | — | — | 542 | — | 74 |
| | 0.1 | | − | 317 | — | — | — | — |

TABLE 7-continued

| Test article | Dose (μg/plate) | S9 Mix | TA98 | Number of revertant colonies | | | |
| --- | --- | --- | --- | --- | --- | --- | --- |
| | | | | TA1537 | TA100 | TA1535 | WP2uvrA |
| ICR-191 | 1.0 | − | — | 1131 | — | — | — |
| SA | 0.5 | − | — | — | — | 222 | — |

—: Not tested
*: Growth inhibition
†: Precipitation
DMSO: Dimethyl sulfoxide
AF-2: 2-(2-Furyl)-3-(5-nitro-2-furyl)acrylamide
SA: Sodium azide
ICR-191: 2-Methoxy-6-chloro-9-[3-(2-chloroethyl)-aminopropylamino]acridine dihydrochloride The number of revertant colonies shows the mean number of each plate.

FORMULATION EXAMPLES

Formulation Examples of the present compound include, for example, the following formulations. The present invention, however, is not intended to be limited to these Formulation Examples.

Formulation Example 1 (Preparation of a Capsule)

| (1) | Compound 1 | 30 mg |
| --- | --- | --- |
| (2) | Microcrystalline cellulose | 10 mg |
| (3) | Lactose | 19 mg |
| (4) | Magnesium stearate | 1 mg |

Ingredients (1), (2), (3), and (4) are mixed to be filled in a gelatin capsule.

Formulation Example 2 (Preparation of a Tablet)

| (1) | Compound 1 | 10 g |
| --- | --- | --- |
| (2) | Lactose | 50 g |
| (3) | Cornstarch | 15 g |
| (4) | Carmellose calcium | 44 g |
| (5) | Magnesium stearate | 1 g |

The total amount of Ingredients (1), (2), and (3) and 30 g of Ingredient (4) are combined with water, dried in vacuo, and then granulated. The resulted granules are mixed with 14 g of Ingredient (4) and 1 g of Ingredient (5), and tableted with a tableting machine. In this manner, 1000 tablets comprising 10 mg of Compound 1 for each tablet are obtained.

INDUSTRIAL APPLICABILITY

A compound of Formula [I] or a pharmaceutically acceptable salt thereof has an SGLT1 inhibitory activity and thus may be useful for the treatment and/or prevention of various disease or conditions that can be expected to be improved by regulating the SGLT1 activity. A compound of Formula [I] or a pharmaceutically acceptable salt thereof may also be useful for the treatment and/or prevention of various diseases or conditions that can be caused by elevated blood glucose level.

The invention claimed is:

1. A compound of Formula [I]:

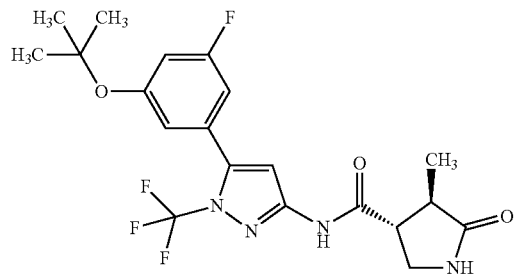

or a pharmaceutically acceptable salt thereof.

2. A pharmaceutical composition comprising the compound according to claim 1 or a pharmaceutically acceptable salt thereof and a pharmaceutically acceptable carrier.

3. A method for inhibiting SGLT1 comprising administering a therapeutically effective amount of the compound according to claim 1 or a pharmaceutically acceptable salt thereof to a mammal.

4. A method for treating diabetes comprising administering a therapeutically effective amount of the compound according to claim 1 or a pharmaceutically acceptable salt thereof to a mammal.

5. The method according to claim 4, wherein the diabetes is type 2 diabetes.

6. A compound of Formula [I]:

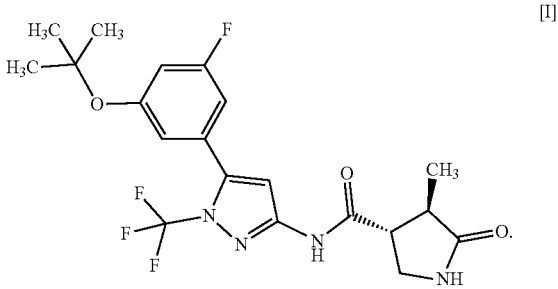 [SMILES: C[C@H]1C(=O)NC[C@@H]1C(=O)Nc1cc(-c2cc(F)cc(OC(C)(C)C)c2)n(C(F)(F)F)n1]

7. A pharmaceutical composition comprising the compound according to claim 6 and a pharmaceutically acceptable carrier.

8. A method for inhibiting SGLT1 comprising administering a therapeutically effective amount of the compound according to claim 6 to a mammal.

9. A method for treating diabetes comprising administering a therapeutically effective amount of the compound according to claim 6 to a mammal.

10. The method according to claim 9, wherein the diabetes is type 2 diabetes.

\* \* \* \* \*

UNITED STATES PATENT AND TRADEMARK OFFICE
CERTIFICATE OF CORRECTION

| | | |
|---|---|---|
| PATENT NO. | : 11,014,910 B2 | Page 1 of 1 |
| APPLICATION NO. | : 16/289500 | |
| DATED | : May 25, 2021 | |
| INVENTOR(S) | : Tomoya Miura et al. | |

It is certified that error appears in the above-identified patent and that said Letters Patent is hereby corrected as shown below:

In the Claims

In Claim 6:
Column 44, Lines 47-61: please replace

" 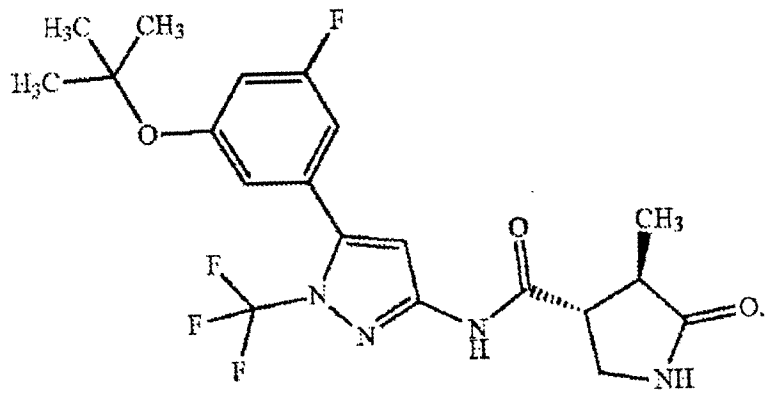 " with

-- 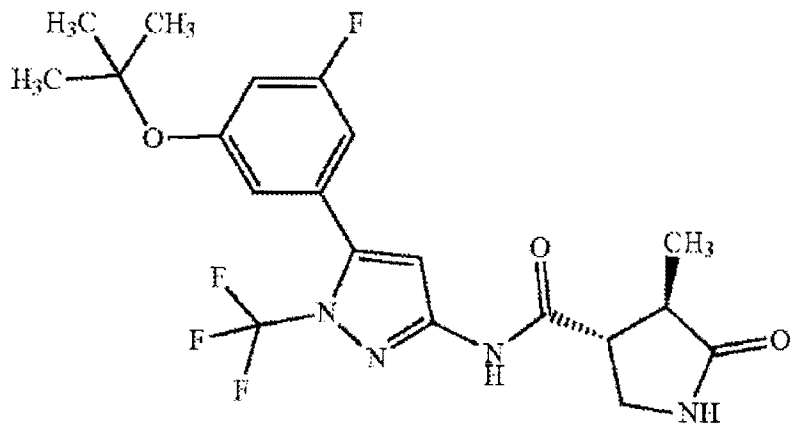 --

Signed and Sealed this
Ninth Day of November, 2021

Drew Hirshfeld
*Performing the Functions and Duties of the*
*Under Secretary of Commerce for Intellectual Property and*
*Director of the United States Patent and Trademark Office*